United States Patent [19]

Ishida et al.

[11] Patent Number: 4,613,717

[45] Date of Patent: Sep. 23, 1986

[54] PROCESS FOR PRODUCING A 1,4-DIALKYLBENZENE

[75] Inventors: Hiroshi Ishida; Hitoshi Nakajima, both of Kurashiki, Japan

[73] Assignee: Research Association for Utilization of Light Oil, Tokyo, Japan

[21] Appl. No.: 741,629

[22] Filed: Jun. 4, 1985

[30] Foreign Application Priority Data

Jun. 25, 1984 [JP] Japan ................................ 59-129169
Jul. 20, 1984 [JP] Japan ................................ 59-149316
Jul. 25, 1984 [JP] Japan ................................ 59-153049

[51] Int. Cl.$^4$ ............................................. C07C 2/66
[52] U.S. Cl. ................................. 585/467; 585/468; 585/475; 502/71; 502/77
[58] Field of Search ............... 585/446, 467, 468, 475, 585/470; 502/71, 77

[56] References Cited

U.S. PATENT DOCUMENTS

| | | | |
|---|---|---|---|
| 4,086,287 | 4/1978 | Kaeding | 260/671 R |
| 4,090,981 | 5/1978 | Rodewald | 252/455 Z |
| 4,145,315 | 3/1979 | Rodewald | 252/455 Z |
| 4,444,989 | 4/1984 | Herkes | 585/467 |
| 4,465,886 | 8/1984 | Rodewald | 585/467 |
| 4,491,678 | 1/1985 | Oda et al. | 585/466 |
| 4,537,757 | 8/1985 | Chono et al. | 502/77 |

OTHER PUBLICATIONS

Niwa, *J. Chem. Soc.*, Chem. Commun., 819–820, 1982.

*Primary Examiner*—Andrew H. Metz
*Assistant Examiner*—A. Pal
*Attorney, Agent, or Firm*—Berman, Aisenberg & Platt

[57] ABSTRACT

By the vapor phase reaction of benzene or a monoalkylbenzene with an alkylating agent in the presence of a specific catalyst obtained by subjecting a zeolite to a treatment with a gas containing a silicic acid ester and then a calcination in an oxygen-containing gas, said zeolite being 10 or more with respect to its molar ratio of $SiO_2/X_2O_3$ in which X is at best one member selected from the group consisting of Al, B and Cr and having a constraint index within the range of 1 to 15, various useful 1,4-dialkylbenzenes can be produced not only in high yield but also in high selectivity.

12 Claims, 10 Drawing Figures

PROCESS FOR PRODUCING A 1,4-DIALKYLBENZENE

This relates to a process for producing a 1,4-dialkylbenzene. More particularly, the present invention is concerned with a process for producing a 1,4-dialkylbenzene by the vapor phase reaction of benzene or a monoalkylbenzene with an alkylating agent in the presence of a specific catalyst obtained by subjecting a zeolite to a treatment with a silicic acid ester and then a calcination in an oxygen-containing gas.

As is well known, 1,4-dialkylbenzenes, such as para-xylene, para-ethyltoluene and para-diethylbenzene, are raw materials for various useful polymer materials. Recently, attention has been drawn to the production of a 1,4-dialkylbenzene by the vapor phase reaction of benzene or a monoalkylbenzene with an alkylating agent in the presence of a catalyst. As the catalyst to be used in the production of the 1,4-dialkylbenzene, there have been proposed a catalyst obtained by treating a crystalline aluminosilicate zeolite ZSM-5, developed by Mobil Oil Corporation, U.S.A., with a variety of metal oxides (hereinafter after referred to as "metal oxide-modified ZSM-5") (U.S. Pat. Nos. 4,086,287 and 4,117,026) and a catalyst obtained by treating mordenite with a silicic acid ester (hereinafter referred to as "modified mordenite") (J.C.S. Chem. Commun. 819 (1982)).

When the above-mentioned metal oxide-modified ZSM-5 is used for the production of a 1,4-dialkylbenzene, a high selectivity for 1,4-dialkylbenzene, e.g. 90–95% based on the produced dialkylbenzenes, can be attained but the yield of the 1,4-dialkylbenzene is extremely low with disadvantages because of its poor catalytic activity. The poor activity of the metal oxide-modified ZSM-5 is attributable to the pores clogged by the metal oxide. The clogging of the pores of ZSM-5 is inevitably caused during the impregnation of ZSM-5 with a metal salt solution for the modification of ZSM-5.

On the other hand, the above-mentioned modified mordenite is relatively high in its catalytic activity but defective in that the selectivity for 1,4-dialkylbenzene based on the produced dialkylbenzenes (hereinafter referred to simply as "selectivity for 1,4-dialkylbenzene") is low (about 78% at the most).

As is apparent from the foregoing, from the commercial point of view, the metal oxide-modified ZSM-5 and modified mordenite both are unsatisfactory as the catalyst for the production of a 1,4-dialkylbenzene from benzene or a monoalkylbenzene.

The present inventors have made extensive and intensive studies with a view to developing a catalyst for the production of a 1,4-dialkylbenzene from benzene or a monoalkylbenzene, by the use of which catalyst a 1,4-dialkylbenzene can be produced not only in high yield but also in high selectivity.

As a result, the present inventors have surprisingly found that when a zeolite, which is 10 or more with respect to its molar ratio of $SiO_2/X_2O_3$ (in which X is at least one member selected from the group consisting of Al, B and Cr) and which has a constraint index within the range of 1 to 15, is treated with a silicic acid ester and the resulting modified zeolite is used as a catalyst for the production of a 1,4-dialkylbenzene from benzene or monoalkylbenzene, the intended 1,4-dialkylbenzene can be produced not only in high yield but also in high selectivity. The present invention has been made based on such a novel finding.

Accordingly, it is an object of the present invention to provide a process for producing a 1,4-dialkylbenzene by the vapor-phase reaction of benzene or a monoalkylbenzene with an alkylating agent in the presence of a catalyst, which can produce the intended 1,4-dialkylbenzene not only in high yield but also in high selectivity.

The foregoing and other objects, features and advantages of the present invention will be apparent to those skilled in the art from the following detailed description taken in connection with the accompanying drawings in which:

Figure 1:
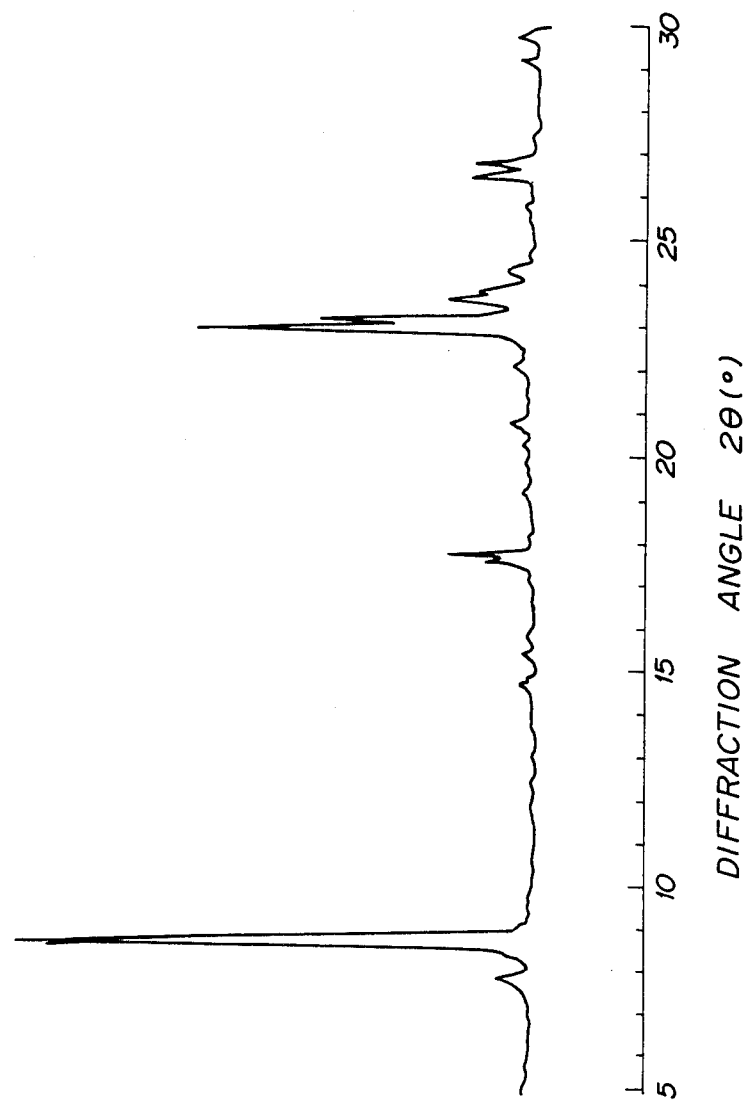
FIG. 1 is an X-ray diffraction pattern of one form of a crystalline aluminosilicate zeolite AZ-1 which may be used as a precursor of the catalyst to be used in the process of the present invention.

In accordance with the present invention, there is provided a process for producing a 1,4-dialkylbenzene which comprises contacting benzene or a monoalkylbenzene with an alkylating agent in the vapor phase in the presence of a catalyst obtained by subjecting a zeolite to a treatment with a gas containing a silicic acid ester and then a calcination in an oxygen-containing gas, said zeolite being 10 or more with respect to its molar ratio of $SiO_2/X_2O_3$ in which X is at least one member selected from the group consisting of Al, B and Cr and having a constraint index within the range of 1 to 15.

Generally, the term "zeolite" is a general term of crystalline aluminosilicates having a rigid three-dimensional network of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra-containing aluminum is balanced by the inclusion in the crystal of a variety of cations. In recent years, there have been prepared a crystalline borosilicate and a crystalline chromosilicate which respectively contain boron atoms and chromium atoms in place of the aluminum atoms. Such borosilicate and chromosilicate have also been regarded as siliceous materials belonging to the category of zeolite. Therefore, the term "zeolite" used in the present invention is intended to mean the siliceous crystalline materials containing at least one member selected from the group consisting of Al, B and Cr, e.g. aluminosilicates, borosilicates and chromosilicates.

The catalyst to be used in the present invention is one obtained by subjecting a zeolite to a treatment with a gas containing a silicic acid ester and then a calcination is an oxygen-containing gas. In this connection, the zeolite which is a precursor of the catalyst to be used in the process of the present invention should be 10 or more with respect to its molar ratio of $SiO_2/X_2O_3$ in which X is as defined above and should have a constraint index of 1 to 15. The molar ratio of $SiO_2/X_2O_3$ (in which X is as defined above) may be determined according to conventional methods using a fluorescent X-ray analyzer. The molar ratio of $SiO_2/X_2O_3$ in which X is as defined above is preferably 10 to 1,000, more preferably 20 to 500.

The term "constraint index" as used in the present invention is intended to mean the ratio of the cracking rate constants for n-hexane and 3-methylpentane. With respect to the constraint index, reference may be made to J. Catal., 67,218 (1981). The constraint index is determined as follows.

A mixture of equal weight of n-hexane and 3-methylpentane (hereinafter often referred to as "hydrocarbon mixture") is diluted with helium to give a mole ratio of helium to the hydrocarbon mixture of 4:1 and is passed over a predetermined amount of a zeolite at a temperature ranging from 260° to 510° C. Then, the amounts of n-hexane and 3-methylpentane remaining unchanged are determined. The constraint index is calculated as follows.

$$\text{Constraint index} = \frac{\log(\text{fraction of n-hexane remaining})}{\log(\text{fraction of 3-methylpentane remaining})}$$

In determining the constraint index, it is necessary to control LHSV (liquid hourly space velocity) so that the overall conversion is 10 to 60%. Usually, the determination of constraint index is carried out at an LHSV of 0.05 to 1.0 $hr^{-1}$.

The constraint index is related to the size of pores of a zeolite. For example, in the case of a zeolite having a twelve-membered ring structure which has a large pore size, the constraint index is one or less. This is so because both n-hexane and 3-methylpentane enter the pores, so that the cracking rate of 3-methylpentane becomes higher than that of n-hexane. On the other hand, in the case of a zeolite having an eight-membered ring structure which has a small pore size, the constraint index is 30 or more because n-hexane molecules are preferentially introduced into the pores and cracked. A zeolite having a ten-membered ring structure such as ZSM-5, has a constraint index value intermediate the constraint indexes of the zeolite having an eight-membered structure and the zeolite having a twelve-membered structure. In this connection, it is to be noted that, even in the case of the same kind of zeolite, the constraint index may vary according to the temperatures employed for determination thereof. For example, when the constraint index of ZSM-5 is determined at temperatures as mentioned above, the obtained values vary within the range of 1 to 12 [J. Catal., 67,218(1981)]. Therefore, it seems to be preferable that the constraint index be determined at a certain fixed temperature. But, in the case of a zeolite having a low activity, the determination at a high temperature is needed because the zeolite does not show activity at a low temperature. On the other hand, in the case of a zeolite having a high activity, the determination at a low temperature is needed because when the determination is carried out at a high temperature the overall conversion of n-hexane and 3-methylpentane exceeds 60%. As is apparent from the foregoing, the constraint indexes of the zeolites having different activities cannot be determined at a certain fixed temperature. But, when the constraint index is determined at temperatures ranging from 260° to 510° C. so that the overall conversion of n-hexane and 3-methylpentane is in the range of 10 to 60%, the constraint index of a zeolite varies but remains within a specific range according to the kind of zeolites. For example, the constraint index of a zeolite having a twelve-membered structure is always less than unity and that of ZSM-5 is always in the range of 1 to 12. The zeolite to be employed in the present invention should have a constraint index in the range of 1 to 15 as determined at a temperature of 260° to 510° C. and at a conversion rate of 10 to 60%.

In the present invention, it is preferable that the zeolite to be used as a precursor catalyst contain hydrogen as a cation in an amount of 5% or more, more preferably 10% or more, particularly preferably 20% or more based on the ion-exchange capacity of the zeolite. The amounts of cations other than hydrogen are not particularly limited.

As examples of the zeolites to be used in the present invention, there may be mentioned crystalline aluminosilicate zeolites, such as AZ-1, ZSM-5 and ZSM-11, crystalline borosilicates, such as AZ-2 and ZSM-5-like borosilicate, and crystalline chromosilicates, such as AZ-3 and ZSM-5-like chromosilicate.

The above-mentioned zeolite AZ-1 has in its X-ray diffraction pattern obtained by using CuKα line at least seven diffraction lines showing the relative intensities at the positions of the respective diffraction angles (2θ) as shown in Table 1 given below.

TABLE 1

| Diffraction angle (2θ, deg) | Relative intensity* |
|---|---|
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 |

Note:
*The intensity of the diffraction line at a diffraction angle of 8.7° ± 0.2° or 8.9° ± 0.2° is taken as 100.

Zeolite AZ-1 can be produced by preparing a mixture of a silica source, an alumina source, an alkali metal source, 1,8-diamino-4-aminomethyloctane, an inorganic acid, such as sulfuric acid and nitric acid, and water and maintaining the mixture at 100° to 200° C. for 10 to 200 hours. AZ-1 is more particularly described in Japanese Patent Application Laid-Open Specification No. 59-128210/1984, the entire contents of which are incorporated herein by reference.

Zeolite ZSM-5 can be produced by preparing a mixture of a silica source, an alumina source, an alkali metal source, a tetrapropylammonium compound, an inorganic acid and water and maintaining the mixture at 100° to 200° C. for 10 to 200 hours. ZSM-5 is more particularly described in U.S. Pat. No. 3,702,886, the entire contents of which are incorporated herein by reference.

Zeolite ZSM-11 can be produced by preparing a mixture of a silica source, an alumina source, an alkali metal source, 1,8-diaminooctane or a tetrabutylammonium compound, an inorganic acid and water and maintaining the mixture at 100° to 200° C. for 10 to 200 hours.

Zeolite ZSM-11 is particularly described in U.S. Pat. No. 3,709,979, the entire contents of which are incorporated herein by reference.

The ZSM-5-like borosilicate can be produced by preparing a mixture of a silica source, a boron oxide source, an alkali metal source, a tetrapropylammonium compound, an inorganic acid and water and maintaining the mixture at 100° to 200° C. for 10 to 200 hours. The ZSM-5-like borosilicate is more particularly described in U.S. Pat. No. 4,269,813, the entire contents of which are incorporated herein by reference.

The ZSM-5-like chromosilicate can be produced by preparing a mixture of a silica source, a chromium source, an alkali metal source, morpholine, an inorganic acid and water and maintaining the mixture at 100° to 200° C. for 10 to 200 hours. The ZSM-5-like chromosilicate is more particularly described in Japanese Patent Application Laid-Open Specification Nos. 57-7817/1982 and 57-169434/1982, the entire contents of which are incorporated herein by reference.

The borosilicate zeolite AZ-2 is particularly described in Japanese Patent Application No. 59-84168/1984, filed Apr. 27, 1984. This zeolite, in the anhydrous state, can be indentified, in terms of mole ratios of oxides, as follows:

$M_{2/n}O \cdot xSiO_2 \cdot yAl_2O_3 \cdot zB_2O_3$ wherein M is at least one cation, n is the valence of the cation, $y+z=1$, $y \geq 0$, $z \geq 0.3$ and $x \geq 5$.

The borosilicate zeolite AZ-2 has in its X-ray diffraction pattern obtained by using CuKα line at least eight diffraction lines showing the relative intensities at the positions of the respective diffraction angles ($2\theta$) as shown in Table 2 given below.

TABLE 2

| Diffraction angle ($2\theta$, deg) | Relative intensity* |
|---|---|
| 7.9 ± 0.2 | 10-50 |
| 8.9 ± 0.2 | 100 |
| 17.7 ± 0.2 | 5-30 |
| 17.9 ± 0.2 | 5-30 |
| 23.2 ± 0.2 | 20-80 |
| 23.4 ± 0.2 | 20-60 |
| 26.7 ± 0.2 | 2-20 |

TABLE 2-continued

| Diffraction angle ($2\theta$, deg) | Relative intensity* |
|---|---|
| 27.0 ± 0.2 | 2-20 |

Note:
*The intensity of the diffraction line at a diffraction angle of 8.9° ± 0.2° is taken as 100.

The borosilicate zeolite AZ-2 can be suitably produced by preparing a mixture of a silica source, an alumina source, a boron oxide source, a sodium source, water and 1,8-diamino-4-aminomethyloctane such that it has the following molar composition:

$Na/SiO_2$: 0.01 to 0.5 (preferably 0.05 to 0.3)
$H_2O/SiO_2$: 2 to 100 (preferably 5 to 50)
1,8-diamino-4-aminomethyl-octane/$SiO_2$: 0.1 to 10 (preferably 0.5 to 5)
$Al_2O_3/SiO_2$: 0 to 0.05 (preferably 0 to 0.02)
$B_2O_3/SiO_2$: 0.005 to 0.5 (preferably 0.01 to 0.1)

and reacting the components of the mixture with one another at a temperature of 100° to 250° C., preferably 120° to 200° C. The reaction time is not critical, and the reaction is carried out for a time sufficient to attain the growth of crystals of AZ-2. Therefore, the reaction time may vary depending on the reaction temperature and the like, but is generally 5 to 200 hours. The thus formed crystals are separated from the reaction mixture by conventional methods, for example, by cooling the whole to room temperature, filtering, water-washing and drying to obtain a crystalline product AZ-2. In the preparation of AZ-2, as the source of silica, there may be mentioned any silica source which is generally used for producing conventional zeolites, for example, a powdered silica, an aqueous solution of sodium silicate, silica sol, etc. Among them, a silica sol is particularly preferably employed. As a sodium source, sodium hydroxide, sodium silicate and the like are generally used. Of them, particularly preferred is sodium hydroxide. As a boron oxide source, there may be mentioned a powdered boron, boric acid, sodium borate and the like. Of them preferred is boric acid. As an alumina source, there may be mentioned any material which is generally employed for producing conventional zeolites, for example, a powdered alumina, aluminum sulfate, sodium aluminate and the like. Even when the above-mentioned alumina source is not used, several hundred parts per million of aluminum are usually contained as an impurity in a silica source and a sodium source as far as the silica source and alumina source are not purified by the special purification method. 1,8-diamino-4-aminomethyloctane is generally obtained by the hydrogeneration of 1,3,6-tricyanohexane in the presence of a hydrogeneration catalyst, such as a Raney catalyst, a catalyst composed of nickel on silica, silica-alumina or the like, a platinum catalyst or a palladium/carbon catalyst, or a reducing agent, such as LiAlH$_4$ [U.S. Pat. No. 3,246,000 and J. Org. Chem., 30 (5) 1351 (1965)]. Further, 1,8-diamino-4-aminomethyloctane may be obtained by the hydrogeneration of 1,3,6-tricyanohexane in the liquid phase using a Raney cobalt as a catalyst and water as a promotor (Japanese Patent Application Publication No. 57-55705/1982). 1,3,6-tricyanohexane, which is a raw material of 1,8-diamino-4-aminomethyloctane, may be prepared by the electrolytic reduction of acrylonitrile or by the reduction of acrylonitrile using sodium amalgam [J. Org. Chem., 30 (5) 1351 (1965) and Japanese Patent Application Publication No. 45-31179/1970].

The chromosilicate zeolite AZ-3 is particularly described in Japanese Patent Application No. 59-81849/1984 filed Apr. 25, 1985. This zeolite, in the anhydrous states, can be identified, in terms of mole ratios of oxides, as follows:

$M_{2/n}O \cdot xSiO_2 \cdot yAl_2O_3 \cdot zCr_2O_3$ wherein M is at least one cation, n is the valence of the cation, $y+z=1$, $y \geqq 0$, $z \geqq 0.3$ and $x \geqq 5$.

The chromosilicate AZ-3 has in its X-ray diffraction pattern obtained by using CuKα line at least nine diffraction lines showing the relative intensities at the positions of the respective diffraction angles (2θ) as shown in Table 3 given below.

TABLE 3

| Diffraction Angle (2θ, deg) | Relative intensity* |
|---|---|
| 7.9 ± 0.2 | 2–10 |
| 8.8 ± 0.2 | 75–100 |
| 8.9 ± 0.2 | 75–100 |
| 17.6 ± 0.2 | 5–25 |
| 17.8 ± 0.2 | 5–25 |
| 23.0 ± 0.2 | 10–28 |
| 23.3 ± 0.2 | 10–25 |
| 26.6 ± 0.2 | 2–20 |
| 26.8 ± 0.2 | 2–20 |

Note:
*The intensity of the diffraction line at a diffraction angle of 8.8° ± 0.2° or 8.9° ± 0.2° is taken as 100.

The chromosilicate AZ-3 can be suitably produced by preparing a mixture of a silica source, an alumina source, a chromia source, a sodium source, water and 1,8-diamino-4-aminomethyloctane such that it has the following molar composition:

$Na/SiO_2$: 0.01 to 0.5 (preferably 0.02 to 0.4)
$H_2O/SiO_2$: 2 to 100 (preferably 5 to 50)
1,8-diamino-4-aminomethyl-octane/$SiO_2$: 0.1 to 10 (preferably 0.5 to 5)
$Al_2O_3/SiO_2$: 0 to 0.05 (preferably 0 to 0.02)
$Cr_2O_3/SiO_2$: 0.0005 to 0.05 (preferably 0.001 to 0.3)

and reacting the components of said mixture with one another at a temperature of 100° to 250° C. The reaction time is not critical, and the reaction is carried out for a time sufficient to attain the growth of crystals of AZ-3. Therefore, the reaction time may vary depending on the reaction temperature and the like, but is generally 5 to 200 hours. The thus formed crystals are separated from the reaction mixture by the conventional methods, for example, by cooling the whole to room temperature, filtering, water-washing and drying to obtain a crystalline product AZ-3.

In the preparation of AZ-3, as the sources of silica, alumina and sodium, the same sources as mentioned above with respect to the preparation of AZ-2 are used. As the source of chromia, there may be mentioned any material which is generally employed for producing conventional chromosilicates, for example, a powdered chromia, chromium nitrate, chromium sulfate and the like.

The catalyst to be used in the process of the present invention is one obtained by subjecting the zeolite of the kind as mentioned above to a treatment with a gas containing a silicic acid ester and then a calcination in an oxygen-containing gas.

As examples of the silicic acid ester to be used in the present invention, there may be mentioned tetramethoxysilane, tetraethoxysilane, tetra-n-propoxysilane, tetra-iso-propoxysilane, tetra-n-butoxysilane and tetra-tert-butoxysilane. Of them, tetramethoxysilane and tetraethoxysilane are particularly preferred. The above-mentioned silicic acid ester is used in the gaseous state. The concentration of the silicic acid ester in the silicic acid ester-containing gas is not critical but is generally 1 to 100 vol %, preferably 5 to 100 vol %. As example of a diluent which may optionally be used for diluting the silicic acid ester, there may be mentioned nitrogen, helium, argon, air, steam and the like. Of them, nitrogen is preferred.

The temperature in treating a zeolite with a silicic acid ester-containing gas is not critical as far as the silicic acid ester can be maintained in a gaseous state at the temperature. The treatment, however, is generally carried out at a temperature in the range of 100° to 500° C., preferably 200° to 400° C. With regard to treating time, it is generally 0.1 to 500 minutes, preferably 1 to 100 minutes, more preferably 20 to 50 minutes.

The pressure in treating a zeolite with a silicic acid ester-containing gas is also not critical as far as the silicic acid ester can be maintained in a gaseous state under the pressure. Thus, the treatment may be carried out under atmospheric pressure, under reduced pressure or under super-atmospheric pressure. The treatment with a silicic acid ester-containing gas may be carried out by any of the batch method and flow method, preferably flow method. In this connection, when the treatment is effected by the flow method, SV (space velocity) on the basis of the silicic acid ester is generally 50 to 50000 hr$^{-1}$, preferably 100 to 10000 hr$^{-1}$, more preferably 500 to 5000 hr$^{-1}$.

The zeolite treated with a silicic acid ester-containing gas is then subjected to a calcination in an oxygen-containing gas. The concentration of oxygen in the oxygen-containing gas is preferably 5 to 100 % by volume, more preferably 10 to 30 % by volume. In general, air is used as the oxygen-containing gas. The calcination temperature is generally 300° to 700° C., preferably 350° to 600° C. The calcination time is generally 10 to 1000 minutes, preferably 20 to 600 minutes, more preferably 30 to 300 minutes.

The amount of silica to be additionally supported on the zeolite by the above-mentioned treatment of the zeolite with a silicic acid ester is preferably at least 0.1 % by weight, more preferably 0.5 to 10 % by weight, based on the untreated zeolite in view of the activity of the resulting catalyst and the selectivity for the intended 1,4-dialkylbenzene.

In the process of the present invention, benzene or a monoalkylbenzene is contacted with an alkylating agent in the vapor phase in the presence of a catalyst of the kind, as mentioned above to produce a 1,4-dialkylbenzene. The monoalkylbenzene to be used in the present invention is preferably a monoalkylbenzene of which the alkyl group has 1 to 3 carbon atoms. Specifically, toluene, ethylbenzene, isopropylbenzene, etc. are preferably employed.

As 1,4-dialkylbenzenes which can be suitably produced in the process of the present invention, there may be mentioned para-xylene, para-ethyltoluene, para-diethylbenzene, para-diisopropylbenzene, paracymene and the like.

As the alkylating agent to be used in the process of the present invention, there may be mentioned an olefin, such as ethylene or propylene and an alcohol such as methanol, ethanol, n-propanol and iso-propanol. Further, when a monoalkylbenzene is used as a starting material and a 1,4-dialkylbenzene is produced by the disproportionation of the monoalkylbenzene, the monoalkylbenzene itself serves as an alkylating agent.

In practicing the present invention, the reaction temperature may widely vary according to the starting materials and the kind of reaction but is generally 200° to 700° C., preferably 300° to 600° C., in view of the selectivity for 1,4-dialkylbenzene and the necessity of keeping the reaction system in a gaseous state.

The vapor phase reaction of benzene or a monoalkylbenzene with an alkylating agent in the presence of a catalyst according to the present invention may be effected in the presence or absence of a diluent. As the diluent, there may be mentioned nitrogen, hydrogen and the like. Of them, hydrogen is particularly preferred because it can advantageously suppress lowering in the activity of the catalyst with time. The molar ratio of a diluent to benzene or a monoalkylbenzene is preferably 0.01 to 100, more preferably 0.1 to 10.

The process of the present invention may be practiced under super-atmospheric pressure, reduced pressure or atmospheric pressure. However, the reaction pressure is preferably in the range of 1 to 20 atm.

Further, the process of the present invention may be preferably effected by the flow method utilizing a fixed catalyst bed or a fluidized catalyst bed.

As described in the foregoing, the process for producing a 1,4-dialkylbenzene according to the present invention is characterized by using a specific catalyst obtained by subjecting a zeolite to a treatment with a gas containing a silicic acid ester and then a calcination in an oxygen-containing gas. By the use of such a specific catalyst, the intended 1,4-dialkylbenzene can be produced not only in high yield but also in high selectivity.

The present invention will now be described in detail with reference to the following Examples that by no means limit the scope of the present invention.

In Examples, the X-ray diffraction patterns of zeolites were determined by using a recording X-ray diffractometer (GEIGERFLEX RAD-IIA manufactured and sold by Rigaku Corporation, Japan).

The $SiO_2/Al_2O_3$ molar ratio and $SiO_2/Cr_2O_3$ molar ratio of a zeolite were determined by using a fluorescent X-ray analyzer (GEIGERFLEX SX-3063P manufactured and sold by Rigaku Corporation, Japan).

The $SiO_2/B_2O_3$ molar ratio of a zeolite was determined as follows. The amount of $SiO_2$ in the zeolite was determined by using a fluorescent X-ray analyzer (GEIGERFLEX SX-3063P manufactured and sold by Rigaku Corporation, Japan). The amount of $B_2O_3$ in the zeolite was determined by using an inductive couples plasma luminescence spectrometer (Model JY 38PII manufactured and sold by Seiko Instruments & Electronics Ltd., Japan). In this connection, prior to the plasma luminescence spectroanalysis, the zeolite was added to a 20 wt % aqueous NaOH solution and heated at 140° C. for 10 hours to dissolve the zeolite in the NaOH solution. The $SiO_2/B_2O_3$ molar ratio was calculated from the above-obtained data with respect to the amounts of $SiO_2$ and $B_2O_3$ in the zeolite.

The amount of $H^+$ in a zeolite was determined as follows. The zeolite was added to a 0.5 N aqueous HCl solution and kept at 50° C. for 24 hours while stirring, thereby to exchange the entire $Na^+$ in the zeolite with $H^+$. Then, the amount of $Na^+$ in the solution was determined by using an inductive couples plasma luminescence spectrometer (Model JY 38PII manufactured and sold by Seiko Instruments & Electronics Ltd., Japan). Separately, the ion-exchange capacity (corresponding to the total amount of Al, B and Cr) of the zeolite was determind by using a fluorescent X-ray analyzer (GEIGERFLEX SX-3063P manufactured and sold by Rigaku Corporation, Japan). The amount of $H^+$ in the zeolite was then calculated by subtracting the amount of $Na^+$ from the ion-exchange capacity of the zeolite.

The amount of silica supported on a zeolite by subjecting the zeolite to a treatment with a gas containing a silicic acid ester and then a calcination in an oxygen-containing gas was calculated by the following equation.

$$SiO_2 \text{ (wt \%)} = \frac{B\,(g) - A\,(g)}{A\,(g)} \times 100$$

wherein A stands for the weight of the zeolite determined before treatment and B the weight of the treated zeolite.

EXAMPLE 1

In 150 g of water were dissolved 100 g of 1,8-diamino-4-aminomethyloctane, 5 g of aluminum sulfate [$Al_2(SO_4)_3 \cdot 18H_2O$] and 5 g of sodium hydroxide to obtain an aqueous solution. Further, 200 g of a silica sol ($SiO_2$ content: 30% by weight) was added to the thus obtained aqueous solution so that a uniform aqueous solution was obtained. Then, 30 g of a 20% by weight aqueous solution of sulfuric acid was dropwise added to the homogeneous aqueous solution under agitation to obtain a uniform gel. The resulting gel was put in a homogenizer and kneaded for 10 minutes at a speed of 10,000 rpm. The kneaded gel was put in a polytetrafluoroethylene-lined stainless steel autoclave and allowed to stand at 180° C. for 45 hours to effect crystallization of the gel.

The crystallization product was filtered off, washed and dried at 120° C. for 6 hours and calcined at 500° C. for 6 hours. The resulting product was subjected to X-ray diffractometry to obtain an X-ray diffraction pattern as shown in FIG. 1. From the pattern, the product was identified as AZ-1. By fluorescent X-ray analysis, the product was found to have a silica/alumina ($SiO_2/Al_2O_3$) ratio of 80. It had a constraint index of 13.0 as measured at 315° C. and contained $H^+$ as a cation in an amount of 60% based on the ion-exchange capacity.

10 g of the thus obtained AZ-1 was formed into 10 to 20 mesh particles and packed in a reaction tube made of a glass. Through the reaction tube was passed a nitrogen gas containing 20% by volume of tetraethoxysilane at 300° C. and at an SV (space velocity) of 1000 hr$^{-1}$ for 20 minutes. Then, air was passed through the tube at 500° C. for 2 hours to effect the calcination of the treated AZ-1.

The amount of silica supported on AZ-1 by the above-mentioned treatment was 2.5 wt % based on the weight of the untreated AZ-1.

The thus obtained treated AZ-1 was used as a catalyst for preparing diethylbenzene from ethylbenzene and ethylene. The reaction was carried out under the following reaction conditions:

| | |
|---|---|
| Ethylbenzene/ethylene/$H_2$ in molar ratio | 5/1/4 |
| WHSV (weight hourly space velocity) (on the basis of ethylbenzene) | 4.0 hr$^{-1}$ |
| Reaction temperature | 350° C. |
| Reaction pressure | 3 kg/cm$^3$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 4 given below.

TABLE 4

| Trap time (hr) | Conversion of ethylbenzene (%) | Selectivity for diethybenzenes based on converted ethylbenzene (%) | Each isomer in diethylbenzenes (%) | | |
|---|---|---|---|---|---|
| | | | p-isomer | m-isomer | o-isomer |
| 2–3 | 22 | 90 | 99.0 | 0.7 | 0.3 |
| 20–21 | 21 | 92 | 99.4 | 0.5 | 0.1 |

EXAMPLE 2

Para-ethyltoluene was prepared from toluene and ethylene using the catalyst as obtained in Example 1 under the following reaction conditions:

| | |
|---|---|
| Toluene/ethylene/$H_2$ in molar ratio | 4/1/4 |
| WHSV (weight hourly space velocity) (on the basis of toluene) | 4.0 $hr^{-1}$ |
| Reaction pressure | 3.0 $kg/cm^2$ |
| Reaction temperature | 400° C. |
| Apparatus | Fixed bed reactor |

There were collected reaction products respectively obtained in a period between 2 hours after the beginning of the reaction and 3 hours after the beginning of the reaction, in a period between 10 hours after the beginning of the reaction and 11 hours after the beginning of the reaction, in a period between 20 hours after the beginning of the reaction and 21 hours after the beginning of the reaction and in a period between 40 hours after the beginning of the reaction and 41 hours after the beginning of the reaction. The thus obtained reaction products each were analyzed by gas chromatography. The results are summarized in Table 5 given below.

TABLE 5

| Trap time (hr) | Conversion of toluene (%) | Selectivity for ethyltoluenes based on converted toluene (%) | Each isomer in ethyltoluenes (%) | | |
|---|---|---|---|---|---|
| | | | p-isomer | m-isomer | o-isomer |
| 2–3 | 18 | 98 | 99.1 | 0.8 | 0.1 |
| 10–11 | 18 | 98 | 99.2 | 0.8 | 0 |
| 20–21 | 17 | 99 | 99.4 | 0.6 | 0 |
| 40–41 | 16 | 99 | 99.5 | 0.5 | 0 |

EXAMPLE 3

The catalyst as obtained in Example 1 was used for disproportionation reaction of toluene. The reaction was carried out under the following reaction conditions:

| | |
|---|---|
| $H^2$/toluene in molar ratio | 2.5 |
| WHSV (weight hourly space velocity) (on the basis of toluene) | 2.0 $hr^{-1}$ |
| Reaction temperature | 500° C. |
| Reaction pressure | 10 $kg/cm^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 6 given below.

TABLE 6

| Trap time (hr) | Conversion of toluene (%) | Selectivity for each product based on converted toluene (mol %) | | | Each isomer in xylenes (%) | | |
|---|---|---|---|---|---|---|---|
| | | Benzene | Xylene | Ethylbenzene | p-isomer | m-isomer | o-isomer |
| 2–3 | 20 | 52.5 | 45.5 | 1.0 | 95.5 | 3.3 | 1.2 |
| 20–21 | 20 | 52.0 | 46.3 | 0.9 | 96.0 | 3.2 | 0.8 |

EXAMPLE 4

The catalyst as obtained in Example 1 was used for disproportionation reaction of ethylbenzene. The reaction was carried out under the following reaction conditions:

| | |
|---|---|
| $H_2$/ethylbenzene in molar ratio | 2.5 |
| WHSV (weight hourly space velocity) (on the basis of ethylbenzene) | 2.0 $hr^{-1}$ |
| Reaction temperature | 350° C. |
| Reaction pressure | 3.0 $kg/cm^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 7 given below.

TABLE 7

| Trap time (hr) | Conversion of ethylbenzene (%) | Selectivity for each product based on converted ethylbenzene (mol %) | | Each isomer in diethylbenzenes (%) | | |
|---|---|---|---|---|---|---|
| | | Benzene | Diethylbenzenes | p-isomer | m-isomer | o-isomer |
| 2–3 | 25 | 55 | 44 | 99.4 | 0.6 | 0 |
| 20–21 | 25 | 54 | 45 | 99.7 | 0.3 | 0 |

EXAMPLE 5

10 g of AZ-1 as obtained in Example 1 was formed into 10 to 20 mesh particles and packed in a reaction tube made of a glass. Through the reaction tube was passed a nitrogen gas containing 25% by volume of tetramethoxysilane at 320° C. and at SV of 1500 hr$^{-1}$ for 20 minutes. Then, air was passed through the tube at 500° C. for 2 hours to effect the calcination of the treated AZ-1.

The amount of silica supported on AZ-1 by the above-mentioned treatment was 3.0 wt % based on the weight of the untreated AZ-1.

The thus obtained treated AZ-1 was used as a catalyst for preparing diethylbenzene from ethylbenzene and ethylene. The reaction was carried out under the following reaction conditions:

| | |
|---|---|
| Ethylbenzene/ethylene in molar ratio | 3.0 |
| WHSV (weight hourly space velocity) (on the basis of ethylbenzene) | 4.0 hr$^{-1}$ |
| Reaction temperature | 360° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of ethylbenzene | 20% |
| Selectivity for diethylbenzenes based on converted ethylbenzene | 90% |
| Para-isomer in diethylbenzenes | 99% |

EXAMPLE 6

The catalyst as obtained in Example 5 was used for preparing xylene from toluene and methanol. The reaction was carried out under the following reaction conditions:

| | |
|---|---|
| Toluene/methanol in molar ratio | 2 |
| WHSV (weight hourly space velocity) (on the basis of toluene) | 4.0 hr$^{-1}$ |
| Reaction temperature | 450° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of toluene | 35% |
| Selectivity for xylenes based on converted toluene | 94% |
| Para-isomer in xylenes | 97% |

EXAMPLE 7

The catalyst as obtained in Example 5 was used for disproportionation reaction of toluene. The reaction was carried out under the following reaction conditions:

| | |
|---|---|
| H$_2$/toluene in molar ratio | 3.0 |
| WHSV (weight hourly space velocity) (on the basis of toluene) | 3.0 hr$^{-1}$ |
| Reaction temperature | 460° C. |
| Reaction pressure | 8.0 kg/cm$^2$ |
| Apparatus | Fixed bed reactor |

The reaction product obtained in a period between 2 hours after the beginning of the reaction and 3 hours after the beginning of the reaction was collected and analyzed by gas chromatography. The results are summarized in Table 8 given below.

TABLE 8

| Trap time (hr) | Conversion of toluene (%) | Selectivity for each product based on converted toluene (mol %) | | | Each isomer in xylenes (%) | | |
|---|---|---|---|---|---|---|---|
| | | Benzene | Xylene | Ethylbenzene | p-isomer | m-isomer | o-isomer |
| 2–3 | 12 | 50.0 | 47.2 | 0.8 | 96.0 | 3.0 | 1.0 |
| 20–21 | 14 | 50.5 | 47.6 | 0.8 | 96.3 | 2.8 | 0.9 |

EXAMPLE 8

In 5000 g of water were dissolved 2000 g of 1,8-diamino-4-aminomethyloctane, 150 g of aluminum sulfate and 150 g of sodium hydroxide to obtain an aqueous solution. Further, 4000 g of a silica sol (SiO$_2$ content: 30% by weight) was added to the obtained aqueous solution to give a uniform aqueous solution. Then, 500 g of a 20% by weight aqueous solution of sulfuric acid was added to the homogeneous aqueous solution under agitation to obtain a uniform gel. The resulting gel was put in a homogenizer and kneaded for 20 minutes at a speed of 10,000 rpm. The kneaded gel was put in a polytetrafluoroethylene-lined stainless steel autoclave and allowed to stand at 165° C. for 60 hours to effect crystallization of the gel.

Figure 2:
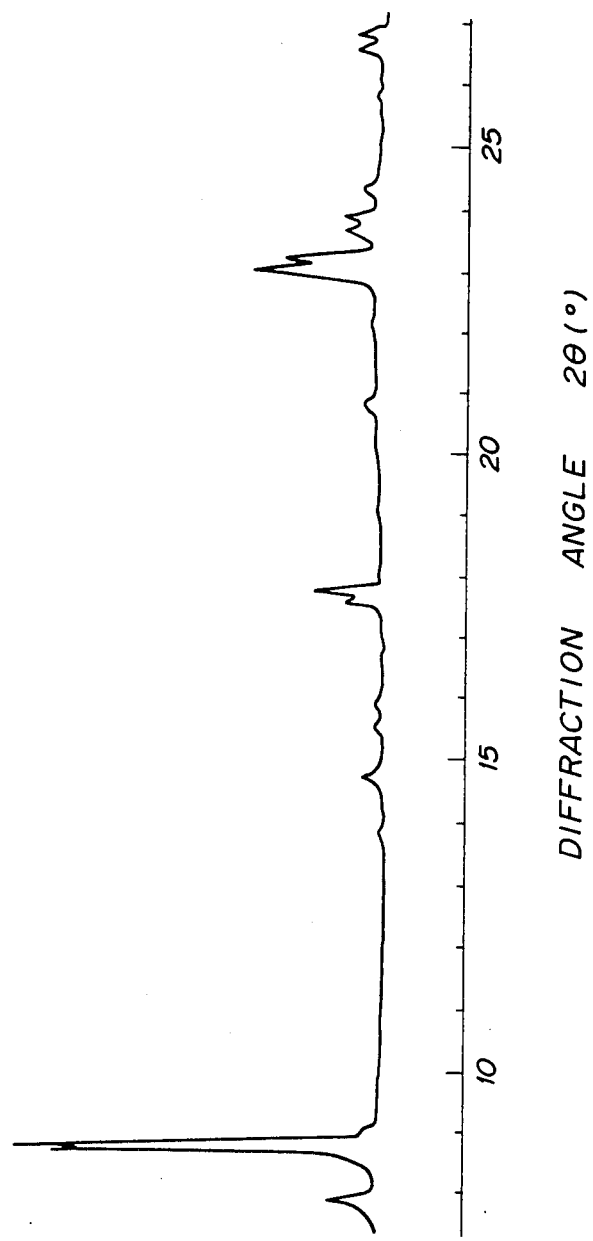
FIG. 2 is an X-ray diffraction pattern of another form of a crystalline aluminosilicate zeolite AZ-1 which may be used as a precursor of the catalyst to be used in the process of the present invention.

The crystallization product was filtered off, washed and dried at 120° C. for 6 hours and calcined at 500° C. for 6 hours. The resulting product was subjected to X-ray diffractometry to obtain an X-ray diffraction pattern as shown in FIG. 2. From the pattern, the product was identified as AZ-1. By fluorescent X-ray analysis, the product was found to have a silica/alumina (SiO$_2$/X$_2$O$_3$) ratio of 45. The product had a constraint index of 13 as measured at 315° C. and contained H$^+$ as a cation in an amount of 70% based on the ion-exchange capacity.

50 g of the thus obtained AZ-1 was formed into 10 to 20 mesh particles and packed in a reaction tube made of a glass. Through the reaction tube was passed a nitrogen gas containing 30% by volume of tetraehoxysilane at 320° C. and at an SV (space velocity) of 2000 hr$^{-1}$ for 25 minutes. Then, air was passed through the tube at 550° C. for 4 hours to effect the calcination of the treated AZ-1.

The amount of silica supported on AZ-1 by the above-mentioned treatment was 2.5 wt % based on the weight of the untreated AZ-1.

The thus obtained treated AZ-1 was used as a catalyst for preparing ethyltoluene from toluene and ethylene.

The reaction was carried out under the following reaction conditions:

| | |
|---|---|
| Toluene/ethylene/H$_2$ in molar ratio | 4/1/4 |
| WHSV (weight hourly space velocity) (on the basis of toluene) | 4.0 hr$^{-1}$ |
| Reaction temperature | 420° C. |
| Reaction pressure | 5 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Tabel 9 given below.

TABLE 9

| Trap time (hr) | Conversion of toluene (%) | Selectivity for ethyltoluenes based on converted toluene (%) | Each isomer in ethyltoluenes (%) | | |
|---|---|---|---|---|---|
| | | | p-isomer | m-isomer | o-isomer |
| 2-3 | 27 | 93 | 97.0 | 2.1 | 0.9 |
| 20-21 | 27 | 94 | 97.6 | 1.7 | 0.7 |

EXAMPLE 9

The catalyst as obtained in Example 8 was used for preparing cymene from toluene and propylene. The reaction was carried out under the following reaction conditions:

| | |
|---|---|
| Toluene/propylene/H$_2$ in molar ratio | 5/1/4 |
| WHSV (weight hourly space velocity) (on the basis of toluene) | 8.0 hr$^{-1}$ |
| Reaction temperature | 320° C. |
| Reaction pressure | 2.0 kg/cm$^2$ |
| Apparatus | Fixed bed reactor |

The reaction product obtained in a period between 2 hours after the beginning of the reaction and 3 hours after the beginning of the reaction and the reaction product obtained in a period between 10 hours after the beginning of the reaction and 11 hours after the beginning of the reaction were each collected and analyzed by gas chromatography. The results are summarized in Table 10 given below.

TABLE 10

| Trap time (hr) | conversion of toluene (%) | Selectivity for cymenes based on converted toluene (%) | Each isomer in cymenes (%) | | |
|---|---|---|---|---|---|
| | | | p-isomer | m-isomer | o-isomer |
| 2-3 | 12 | 90 | 96.5 | 3.2 | 0.3 |
| 10-11 | 12 | 91 | 97.0 | 3.0 | 0 |

EXAMPLE 10

20 g of AZ-1 as obtained in Example 8 was formed into 10 to 20 mesh particles and packed in a reaction tube made of a glass. Through the reaction tube was passed a nitrogen gas containing 8% by volume of tetramethoxysilane at 200° C. and at an SV (space velocity) of 3000 hr$^{-1}$ for 10 minutes. Then, air was passed through the tube at 500° C. for 3 hours to effect the calcination of the treated AZ-1.

The amount of silica supported on AZ-1 by the above-mentioned treatment was 0.5 wt % based on the weight of the untreated AZ-1.

The thus obtained treated AZ-1 was used as a catalyst for preparing diethylbenzene from ethylbenzene and ethylene. The reaction was carried out under the following reaction conditions:

| | |
|---|---|
| Ethylbenzene/ethylene in molar ratio | 4.0 |
| WHSV (weight hourly space velocity) (on the basis of ethylbenzene) | 3.0 hr$^{-1}$ |
| Reaction temperature | 350° C. |
| Reaction pressure | Atmospheric |
| Apparatus | Fixed bed reactor |

The reaction product obtained in a period between 3 hours after the beginning of the reaction and 4 hours after the beginning of the reaction was collected and analyzed by gas chromatography. The results are summarized below.

| | |
|---|---|
| Conversion of ethylbenzene | 10% |
| Selectivity for diethylbenzenes based on converted ethylbenzene | 92% |
| Para-isomer in diethylbenzenes | 96% |

EXAMPLE 11

In 350 g of water were dissolved 5 g of aluminum sulfate and 10 g of tetrapropylammonium bromide, and further was added 150 g of a Q brand silicate aqueous solution (Na$_2$O, 8.9 wt % ; SiO$_2$, 28.9 wt % ; H$_2$O, 62.2 wt %). The resulting mixture was stirred to give a uniform gel. To the gel was dropwise added 50 g of a 20% aqueous solution of sulfuric acid under agitation to accelerate the gelation. The resulting gel was put in a polytetrafluoroethylene-lined stainless steel autoclave and stirred at 150° C. for 20 hours to effect crystallization of the gel.

The crystallization product was filtered off, washed and dried at 120° C. for 3 hours and calcined at 500° C. for 4 hours.

Figure 3:
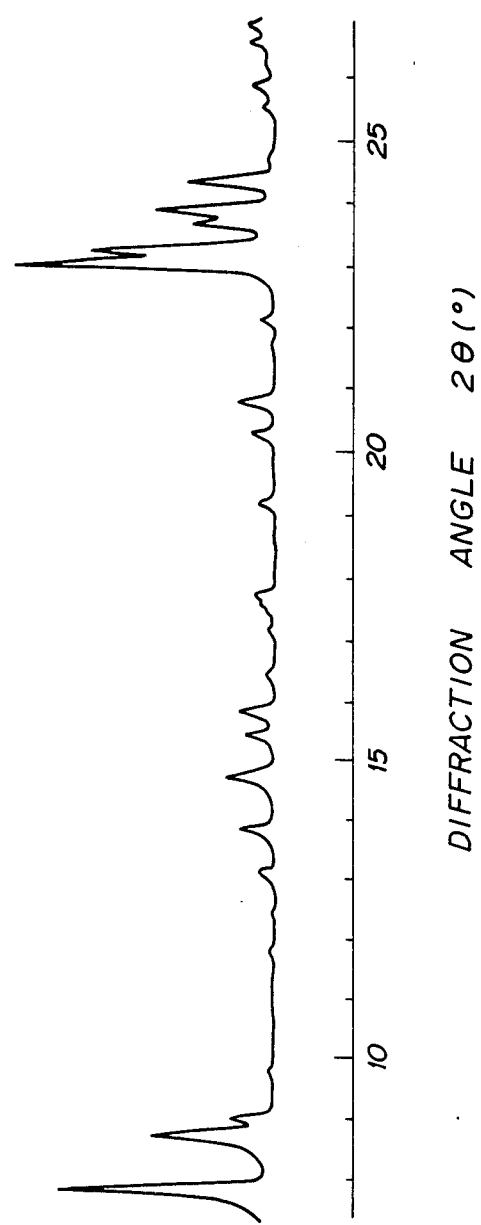
FIG. 3 is an X-ray diffraction pattern of a crystalline aluminosilicate zeolite ZSM-5 which may be used as a precursor of the catalyst to be used in the process of the present invention.

The resulting product was subjected to X-ray diffractometry to obtain an X-ray diffraction pattern as shown in FIG. 3. From the pattern, the product was identified as ZSM-5. By fluorescent X-ray analysis, the product was found to have a silica/alumina (SiO$_2$/Al$_2$O$_3$) ratio of 50. It had a constraint index of 10.5 as measured at 320° C. and contained H$^+$ as a cation in an amount of 85% based on the ion-exchange capacity. 10 g of the thus obtained ZSM-5 was formed into 10 to 20 mesh particles and packed in a reaction tube made of a glass. Through the reaction tube was passed a nitrogen gas containing 20% by volume of tetraethoxysilane at 300° C. and at an SV (space velocity) of 1000hr$^{-1}$ for 40 minutes. Then, air was passed through the tube at 500° C. for 3 hours to effect the calcination of the treated ZSM-5.

The amount of silica supported on ZSM-5 by the above-mentioned treatment was 6.2 wt % based on the weight of the untreated ZSM-5.

The thus obtained treated ZSM-5 was used as a catalyst for disproportionation reaction of ethylbenzene. The reaction was carried out under the following reaction conditions:

| H$_2$/ethylbenzene in molar ratio | 3.0 |
|---|---|
| WHSV (weight hourly space velocity) (on the basis of ethylbenzene) | 2.0 hr$^{-1}$ |
| Reaction Temperature | 340° C. |
| Reaction Pressure | 2.0 kg/cm$^2$ |
| Apparatus | Fixed bed reactor |

The reaction product obtained in a period between 2 hours after the beginning of the reaction and 3 hours after the beginning of the reaction and the reaction product obtained in a period between 10 hours after the beginning of the reaction and 11 hours after the beginning of the reaction were each collected and analyzed by gas chromatography. The results are summarized in Table 11 given below.

TABLE 11

| Trap time (hr) | Conversion of ethylbenzene (%) | Selectivity for each product based on converted ethylbenzene (mol %) | | Each isomer in diethylbenzenes (%) | | |
|---|---|---|---|---|---|---|
| | | Benzene | Diethylbenzene | p-isomer | m-isomer | o-isomer |
| 2–3 | 10 | 54.5 | 45.0 | 95.0 | 4.2 | 0.8 |
| 10–11 | 10 | 54.2 | 45.8 | 95.2 | 4.3 | 0.5 |

EXAMPLE 12

In 150 g of water were dissolved 100 g of octamethylenediamine, 5 g of aluminum sulfate and 5 g of sodium hydroxide to give a homogeneous solution. To the solution was added 200 g of a silica sol (SiO$_2$ content: 30% by weight), and further was dropwise added 20 g of a 20% by weight aqueous solution of sulfuric acid under agitation to obtain a uniform gel. The resulting gel was put in a polytetrafluoroethylene-lined stainless steel autoclave and allowed to crystallize under agitation at 150° C. for 40 hours.

Figure 4:
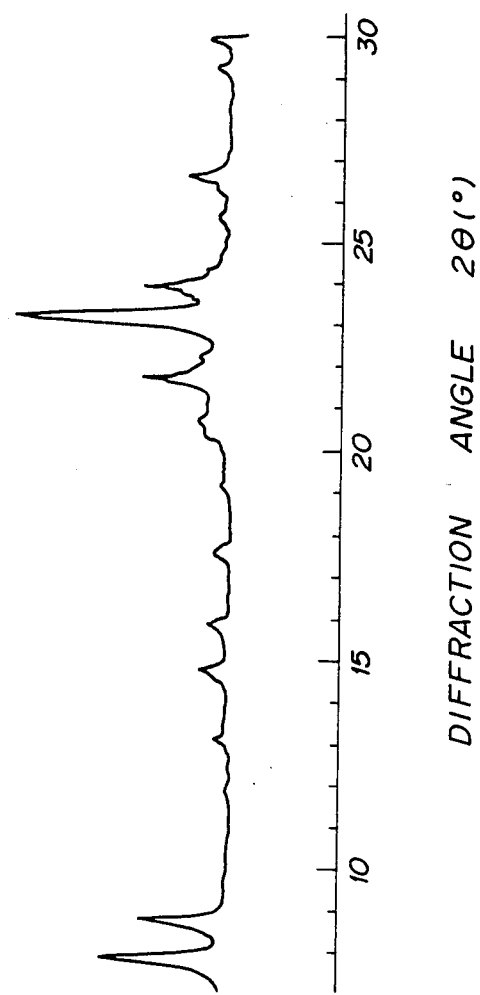
FIG. 4 is an X-ray diffraction pattern of a crystalline aluminosilicate zeolite ZSM-11 which may be used as a precursor of the catalyst to be used in the process of the present invention.

The crystallization product was filtered off, washed, dried at 120° C. for 3 hours and calcined at 500° C. for 4 hours. The resulting product was subjected to X-ray diffractometry to obtain an X-ray diffraction pattern as shown in FIG. 4. From the pattern the product was identifed as ZSM-11. By fluorescent X-ray analysis, the product was found to have a silica/alumina molar ratio of 30. It had a constraint index of 9.0 as measured at 320° C. and contained H+ as a cation in an amount of 80% based on the ion-exchange capacity.

20 g of the thus obtained ZSM-11 was formed into 10 to 20 mesh particles and packed in a reaction tube made of a glass. Through the reaction tube was passed a nitrogen gas containing 15% by volume of tetramethoxysilane at 300° C. and at an SV (space velocity) of 1300 hr$^{-1}$ for 30 minutes. Then, air was passed through the tube at 500° C. for 2 hours to effect the calcination of the treated ZSM-11.

The amount of silica supported on ZSM-5 by the above-mentioned treatment was 6.5 wt % based on the weight of the untreated ZSM-11.

The obtained treated ZSM-11 was used as a catalyst for preparing diethylbenzene from ethylbenzene and ethylene. The reaction was carried out under the following reaction conditions:

| Ethylbenzene/ethylene in molar ratio | 2.8 |
|---|---|
| WHSV (weight hourly space velocity) (on the basis of ethylbenzene) | 4.0 hr$^{-1}$ |
| Reaction temperature | 350° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| Conversion of ethylbenzene | 30% |
|---|---|
| Selectivity for diethylbenzenes based on converted ethylbenzene | 92% |
| Para-isomer in diethylbenzenes | 95% |

EXAMPLE 13

In 34 g of water were dissolved 20 g of 1.8-diamino-4-aminomethyloctane, 0.5 g of boric acid (H$_3$BO$_3$) and 1 g of sodium hydroxide, and further was added 40 g of a silica sol (SiO$_2$ content: 30% by weight) to obtain a uniform solution. To the obtained solution was dropwise added 8 g of a 20% aqueous solution of sulfuric acid under agitation to give a uniform gel. The resulting gel was put in a homogenizer and kneaded at a speed of 10,000 rpm. Then, the gel was put in a polytetrafluoroethylene-lined autoclave and allowed to stand at 180° C. for 70 hours to effect crystallization of the gel.

Figure 5:
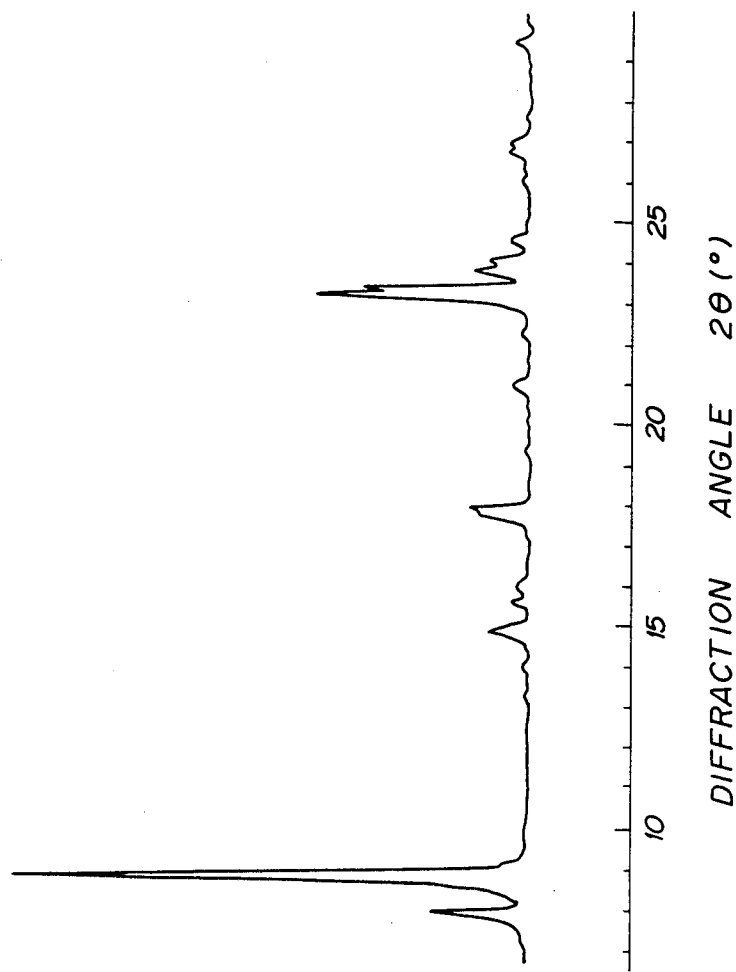
FIG. 5 is an X-ray diffraction pattern of one form of a crystalline borosilicate zeolite AZ-2 which may used as a precursor of the catalyst to be used in the process of the present invention.

The crystallization product was filtered off, washed and dried at 120° C. and calcined in air at 500° C. for 6 hours. The resulting product was subjected to X-ray diffractometry to obtain an X-ray diffraction pattern as shown in FIG. 5. From the pattern, the product was identified as AZ-2.

Further, the thus obtained AZ-2 was subjected to ion-exchange in a 0.5 N hydrochloric acid for 24 hours. Then, the product was filtered off, washed, dried at 120° C. for 4 hours, and calcined in air at 500° C. for 4 hours to obtain an ion-exchanged AZ-2 (H-AZ-2). The resulting H-AZ-2 had an SiO$_2$/B$_2$O$_3$ molar ratio of 30 and a constraint index of 12.5 as measured at 330° C. and contained H+as a cation in an amount of 95% based on the ion-exchange capacity.

10 g of the obtained ion-exchanged borosilicate H-AZ-2 was formed into 10 to 20 mesh particles and packed in a reaction tube made of a glass. Through the reaction tube was passed a nitrogen gas containing 20% by volume of tetraethoxysilane at 300° C. and at an SV of 10000 hr.$^{-1}$ for 20 minutes. Then, air was passed through the tube at 500° C. for 2 hours to effect the calcination of the treated AZ-2.

The amount of silica supported on H-AZ-2 by the above-mentioned treatment was 1.3 wt % based on the weight of the untreated H-AZ-2.

The thus obtained treated H-AZ-2 was used as a catalyst for preparing diethylbenzene from ethylbenzene and ethylene. The reaction was carried out using 2 g of the catalyst under the following reaction conditions:

| | |
|---|---|
| Ethylbenzene/ethylene in molar ratio | 3.0 |
| WHSV (weight hourly space velocity) (on the basis of ethylbenzene) | 4.0 hr$^{-1}$ |
| Reaction temperature | 350° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of ethylbenzene | 22% |
| Selectivity for diethylbenzenes based on converted ethylbenzene | 96% |
| Para-isomer in diethylbenzenes | 97% |

EXAMPLE 14

The catalyst as obtained in Example 13 was used for preparing ethyltoluene from toluene and ethylene. The reaction was carried out under the following reaction conditions:

| | |
|---|---|
| Toluene/ethylene/H$_2$ in molar ratio | 6/1/5 |
| WHSV (weight hourly space velocity) (on the basis of toluene) | 4.0 hr$^{-1}$ |
| Reaction temperature | 400° C. |
| Reaction pressure | 4.0 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 12 given below.

TABLE 12

| Trap time (hr) | Conversion toluene (%) | Selectivity for ethyltoluenes based on converted toluene (%) | Each isomer in ethyltoluenes (%) | | |
|---|---|---|---|---|---|
| | | | p-isomer | m-isomer | o-isomer |
| 2-3 | 14 | 98 | 38.0 | 1.5 | 0.5 |
| 20-21 | 14 | 98 | 98.2 | 1.5 | 0.3 |

EXAMPLE 15

The catalyst as obtained in Example 13 was used for disproportionation reaction of toluene. The reaction was carried out under the following reaction conditions:

| | |
|---|---|
| H$_2$/toluene in molar ratio | 3.0 |
| WHSV (weight hourly space velocity) (on the basis of toluene) | 2.0 hr$^{-1}$ |
| Reaction temperature | 500° C. |
| Reaction pressure | 10 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 13 given below.

TABLE 13

| Trap time (hr) | Conversion of toluene (%) | Selectivity for each product based on converted toluene (mol %) | | | Each isomer in xylenes | | |
|---|---|---|---|---|---|---|---|
| | | Benzene | Xylene | Ethylbenzene | p-isomer | m-isomer | o-isomer |
| 2-3 | 13 | 51.5 | 47.1 | 0.9 | 94.5 | 4.5 | 1.0 |
| 20-21 | 13 | 51.4 | 47.0 | 1.0 | 95.0 | 4.2 | 0.8 |

EXAMPLE 16

The catalyst as obtained in Example 13 was used for preparing xylene from toluene and methanol. The reaction was carried out under the following reaction conditions:

| | |
|---|---|
| Toluene/methanol in molar ratio | 4 |
| WHSV (weight hourly space velocity) (on the basis of toluene) | 4.0 hr$^{-1}$ |
| Reaction temperature | 500° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of toluene | 20% |
| Selectivity for xylenes based on converted toluene | 95% |
| Each isomer in xylenes: | |
| Para-isomer | 95% |
| Meta-isomer | 4% |
| Ortho-isomer | 1% |

EXAMPLE 17

10 g of the ion-exchanged crystalline borosilicate H-AZ-2 as obtained in Example 13 was formed into 10 to 20 mesh particles and packed in a reaction tube made of a glass. Through the reaction tube was passed a nitrogen gas containing 25% by volume of tetramethoxysilane at 320° C. and at an SV of 1500 hr$^{-1}$ for 20 minutes. Then, air was passed through the reaction tube at 500° C. for 2 hours to effect the calcination of the treated H-AZ-2.

The amount of silica supported on H-AZ-2 by the above-mentioned treatment was 0.8 wt % based on the weight of the untreated H-AZ-2.

The thus obtained treated H-AZ-2 was used as a catalyst for preparing diethylbenzene from ethylbenzene and ethylene. The reaction was carried out under the following reaction conditions:

| | |
|---|---|
| Ethylbenzene/ethylene/$H_2$ in molar ratio | 5/1/4 |
| WHSV (weight hourly space velocity) (on the basis of ethylbenzene) | 4.0 $hr^{-1}$ |
| Reaction tempeature | 350° C. |
| Reaction pressure | 3 $kg/cm^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 14 given below.

TABLE 14

| Trap time (hr) | Conversion of ethylbenzene (%) | Selectivity for diethylbenzenes based on converted ethylbenzene (%) | Each isomer in diethylbenzenes | | |
|---|---|---|---|---|---|
| | | | p-isomer | m-isomer | o-isomer |
| 2-3 | 20 | 94 | 96.5 | 3.0 | 0.5 |
| 20-21 | 20 | 94 | 96.8 | 2.8 | 0.4 |

EXAMPLE 18

The catalyst as obtained in Example 17 was used for disproportionation reaction of toluene. The disproportionation reaction was carried out under the following reaction conditions:

| | |
|---|---|
| $H_2$/toluene in molar ratio | 4.0 |
| WHSV (weight hourly space velocity) (on the basis of toluene) | 3.0 $hr^{-1}$ |
| Reaction temperature | 480° C. |
| Reaction pressure | 9.0 $kg/cm^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 15 given below.

TABLE 15

| Trap time (hr) | Conversion of toluene (%) | Selectivity for each product based on converted toluene (mol %) | | | Each isomer in xylenes (%) | | |
|---|---|---|---|---|---|---|---|
| | | Benzene | Xylene | Ethylbenzene | p-isomer | m-isomer | o-isomer |
| 2-3 | 12 | 51.5 | 46.8 | 0.9 | 94.7 | 4.0 | 1.3 |
| 20-21 | 12 | 51.8 | 47.1 | 0.9 | 95.0 | 4.0 | 1.0 |

EXAMPLE 19

The catalyst as obtained in Example 17 was used for preparing cymene from toluene and propylene. The reaction was carried out under the following reaction conditions:

| | |
|---|---|
| Toluene/propylene/$H_2$ in molar ratio | 5/1/4 |
| WHSV (weight hourly space velocity) (on the basis of toluene) | 8.0 $hr^{-1}$ |
| Reaction temperature | 320° C. |
| Reaction pressure | 2.0 $kg/cm^2$ |
| Apparatus | Fixed bed reactor |

The reaction product obtained in a period between 2 hours after the beginning of the reaction and 3 hours after the beginning of the reaction and the reaction product obtained in a period between 10 hours after the beginning of the reaction and 11 hours after the beginning of the reaction were each collected and analyzed by gas chromatography. The results are summarized in Table 16 given below.

TABLE 16

| Trap time (hr) | Conversion of toluene (%) | Selectivity for cymenes based on converted toluene (%) | Each isomer in cymenes (%) | | |
|---|---|---|---|---|---|
| | | | p-isomer | m-isomer | o-isomer |
| 2—3 | 10 | 91 | 95.0 | 4.2 | 0.8 |
| 10-11 | 10 | 92 | 96.0 | 3.5 | 0.5 |

EXAMPLE 20

In 400 g of water were dissolved 250 g of 1,8-diamino-4-aminomethyloctane, 5 g of boric acid and 10 g of sodium hydroxide, and further was added 50 g of a silica sol ($SiO_2$ content: 30% by weight) to obtain a uniform solution. To the solution was dropwise added 60 g of a 20% by weight aqueous solution of sulfuric acid to obtain a uniform gel. The obtained gel was put in a homogenizer and kneaded at a speed of 10,000 rpm. Then, the gel was put in a polytetrafluoroethylene-lined autoclave and allowed to stand at 170° C. for 80 hours to effect crystallization of the gel.

Figure 6:
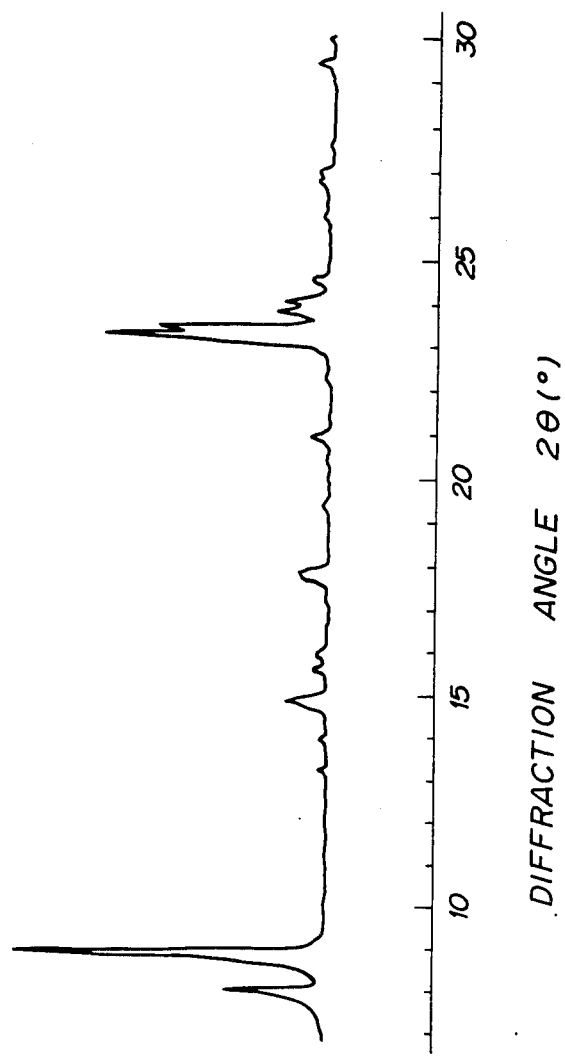
FIG. 6 is an X-ray diffraction pattern of another form of a crystalline borosilicate zeolite AZ-2 which may be used as a precursor of the catalyst to be used in the process of the present invention.

The obtained crystallization product was filtered off, washed and dried at 120° C. for 4 hours and calcined at 500° C. for 8 hours. The resulting product was subjected to X-ray diffractometry to obtain an X-ray diffraction pattern as shown in FIG. 6. From the pattern, the product was identified as a crystalline borosilicate AZ-2.

Further, the thus obtained AZ-2 was subjected to ion-exchange in a 0.5 N hydrochloric acid for 24 hours. The product was filtered off, washed and dried at 120° C. for 4 hours and calcined in air at 500° C. for 4 hours to obtain an ion-exchanged AZ-2 (H-AZ-2). Then, the H-AZ-2 was subjected to chemical analysis and found to have an $SiO_2/B_2O_3$ molar ratio of 60. The product had a constraint index of 11.8 as measured at 330° C. and contained $H^+$ as a cation in an amount of 92% based on the ion-exchange capacity.

20 g of the thus obtained H-AZ-2 was formed into 10 to 20 mesh particles, and packed in a reaction tube made of a glass. Through the reaction tube was passed a nitrogen gas containing 10% by volume of tetraethoxysilane at 250° C. and at an SV of 1,000 hr$^{-1}$ for 20 minutes. Then, air was passed through the tube at 550° C. for 4 hours to effect the calcination of the treated H-AZ-2.

The amount of silica supported on H-AZ-2 by the above-mentioned treatment was 2.0 wt% based on the weight of the untreated H-AZ-2.

The thus obtained treated H-AZ-2 was used as a catalyst for disproportionation reaction of ethylbenzene. The reaction was carried out under the following reaction conditions:

| | |
|---|---|
| H$_2$/ethylbenzene in molar ratio | 4.0 |
| WHSV (weight hourly space velocity) (on the basis of ethylbenzene) | 5.0 hr$^{-1}$ |
| Reaction temperature | 350° C. |
| Reaction pressure | 3.0 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 17 given below.

TABLE 17

| Trap time (hr) | Conversion of ethylbenzene (%) | Selectivity for each product based on converted ethylbenzene (mol %) | | Each isomer in diethylbenzenes (%) | | |
|---|---|---|---|---|---|---|
| | | Benzene | Diethylbenzenes | p-isomer | m-isomer | o-isomer |
| 2-3 | 45 | 53.5 | 45.5 | 98.0 | 1.5 | 0.5 |
| 20-21 | 44 | 53.8 | 45.7 | 98.6 | 1.2 | 0.2 |

EXAMPLE 21

2.0 g of boric acid, 18 g of concentrated sulfuric acid and 27 g of tetrapropylammonium bromide were dissolved in 250 ml of water to prepare Solution A. Separately, 200 g of water glass (SiO$_2$, 29% by weight; Na$_2$O, 9.4% by weight; water, 61.6% by weight) was dissolved in 250 ml of water to prepare Solution B. Then, Solutions A and B were simultaneously added dropwise to a solution, prepared by adding 80 g of sodium chloride to 130 ml of water, over a period of about 10 minutes. To the resulting solution was added sulfuric acid to adjust the pH of the solution to 9.5. The thus obtained solution was put in a polytetrafluoroethylene-lined autoclave and allowed to stand at 170° C. for 24 hours to effect crystallization of the solution.

Figure 7:
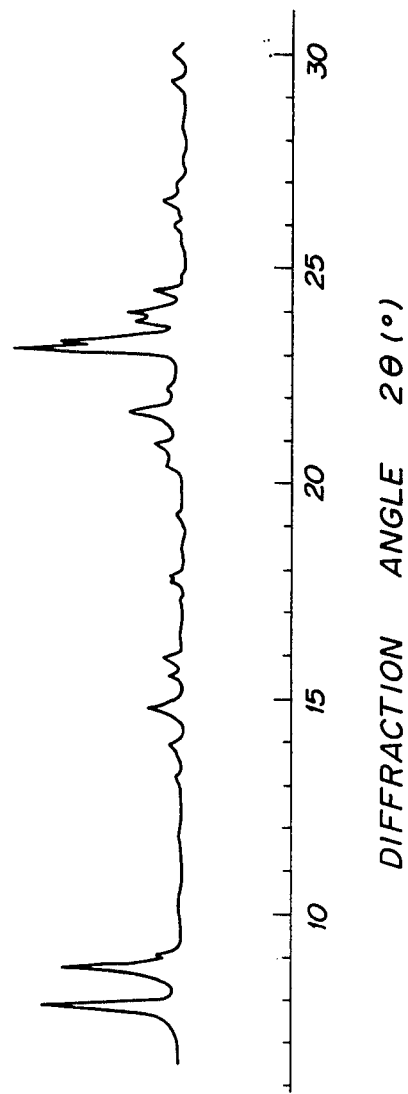
FIG. 7 is an X-ray diffraction pattern of a crystalline ZSM-5-like borosilicate zeolite which may be used as a precursor of the catalyst to be used in the process of the present invention.

The crystallization product was filtered off, washed and dried at 120° C. for 6 hours and calcined at 500° C. for 6 hours. The resulting product was subjected to X-ray diffractometry to obtain an X-ray diffraction pattern as shown in FIG. 7. From the pattern, the product was identified as a ZSM-5-like borosilicate disclosed in USP 4,269,813.

The calcined crystallization product was subjected to ion-exchange for 24 hours in a 1 N aqueous solution of ammonium chloride, filtered off, washed and dried at 120° C. for 4 hours and calcined in air at 500° C. for 4 hours. The thus obtained product was subjected to chemical analysis and found to have an SiO$_2$/B$_2$O$_3$ molar ratio of 40. The product had a constraint index of 9.5 as measured at 320° C. and contained H$^+$ as a cation in an amount of 97% based on the ion-exchange capacity.

10 g of the thus obtained ion-exchanged crystalline borosilicate was formed into 10 to 20 mesh particles and packed in a reaction tube made of a glass. Through the reaction tube was passed a nitrogen gas containing 15% by volume of tetraethoxysilane at 350° C. and at an SV of 2000 hr$^{-1}$ for 25 minutes. Then, air was passed through the tube at 550° C. for 2 hours to effect the calcination of the treated borosilicate.

The amount of silica supported on the ion-exchanged borosilicate by the above-mentioned treatment was 3.5 wt % based on the weight of the untreated ion-exchanged borosilicate.

The thus obtained treated borosilicate was used as a catalyst for preparing diethylbenzene from ethylbenzene and ethylene. The reaction was carried out under the following reaction conditions:

| | |
|---|---|
| Ethylbenzene/ethylene/H$_2$ in molar ratio | 5/1/4 |
| WHSV (weight hourly space velocity) (on the basis of ethylbenzene) | 4.0 hr$^{-1}$ |
| Reaction temperature | 350° C. |
| Reaction pressure | 3.5 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 18 given below.

TABLE 18

| Trap time (hr) | Conversion of ethylbenzene (%) | Selectivity for diethylbenzenes based on converted ethylbenzene (%) | Each isomer in diethylbenzenes (%) | | |
|---|---|---|---|---|---|
| | | | p-isomer | m-isomer | o-isomer |
| 2-3 | 20 | 89 | 94.6 | 4.4 | 1.0 |
| 20-21 | 20 | 90 | 95.0 | 4.3 | 0.7 |

EXAMPLE 22

In 340 g of water were dissolved 200 g of 1,8-diamino-4-aminomethyloctane, 5 g of chromium nitrate [Cr(NO$_3$)$_3$.9H$_2$O] and 10 g of sodium hydroxide, and further was added 400 g of a silica sol (SiO$_2$ content: 30% by weight) to obtain a uniform solution. To the resulting solution was dropwise added 60 g of a 20% solution of sulfuric acid under agitation to obtain a uniform gel. The obtained gel was put in a homogenizer and kneaded at a speed of 10000 rpm. Then, the gel was put in a polytetrafluoroethylene-lined autoclave and allowed to stand at 180° C. for 60 hours to effect crystallization.

Figure 8:
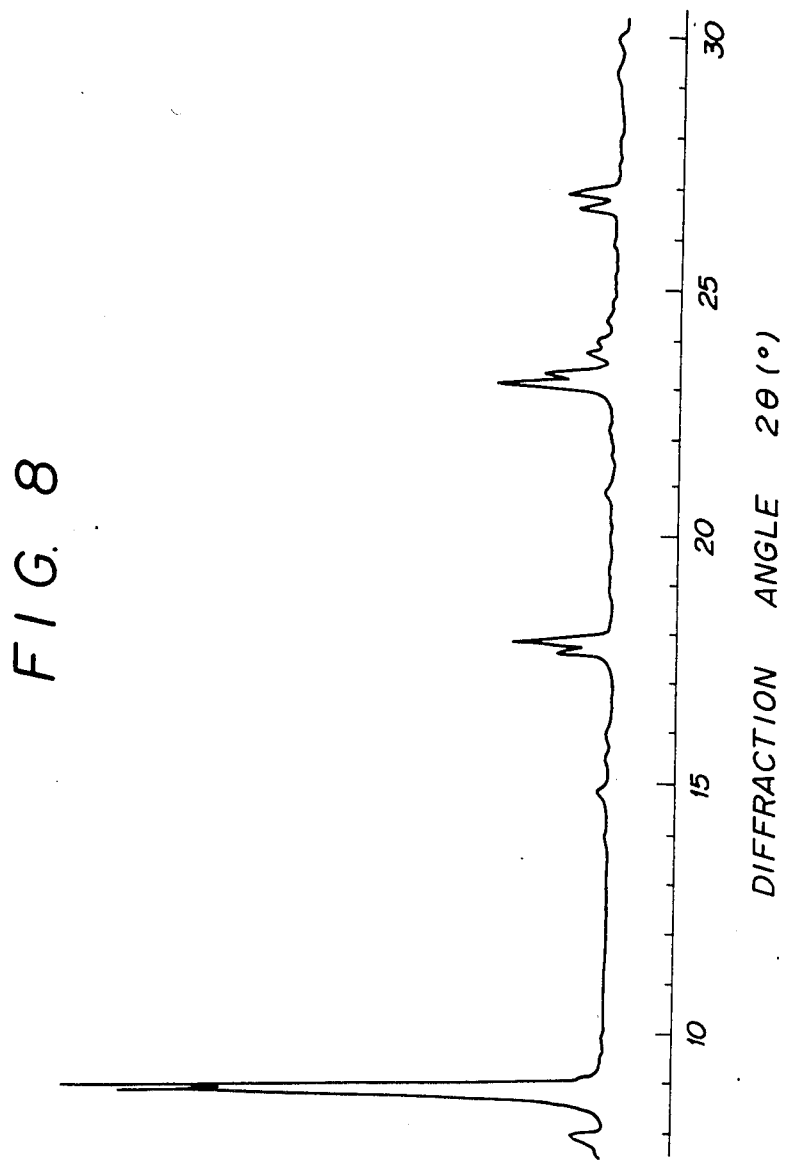
FIG. 8 is an X-ray diffraction pattern of one form of a crystalline chromosilicate zeolite AZ-3 which may be used as a precursor of the catalyst to be used in the process of the present invention.

The obtained product was filtered out, washed and dried at 120° C. for 10 hours and calcined in air at 500° C. for 6 hours. The product was subjected to X-ray diffractometry to obtain an X-ray diffraction pattern as shown in FIG. 8. From the X-ray diffraction pattern the product was identified as a crystalline chromosilicate AZ-3.

The thus obtaine AZ-3 was subjected to ion-exchange in a 0.5 N hydrochloric acid solution for 24 hours. Then, the product was filtered off, washed and dried at 120° C. for 10 hours and calcined in air at 500°

C. for 6 hours to obtain an ion-exchanged AZ-3 (H-AZ-3).

The H-AZ-3 had an $SiO_2/Cr_2O_3$ molar ratio of 20 and a constraint index of 13.5 as measured at 335° C. and contained $H^+$ as a cation in an amount of 95% based on the ion-exchange capacity.

10 g of the above-obtained H-AZ-3 was formed into 10 to 20 mesh particles and filled in a reaction tube made of a glass. Through the reaction tube was passed a nitrogen gas containing 20% by volume of tetraethoxysilane at 300° C. and at an SV of 1000 $hr^1$ for 20 minutes. Then, air was passed through the tube at 500° C. for 2 hours to effect the calcination of the treated H-AZ-3.

The amount of silica supported on H-AZ-3 by the above-mentioned treatment was 1.0 wt % based on the weight of the untreated H-AZ-3.

The thus obtained treated H-AZ-3 was used as a catalyst for preparing diethylbenzene from ethylbenzene and ethylene. The reaction was carried out under the following reaction conditions:

| | |
|---|---|
| Ethylbenzene/ethylene in molar ratio | 2.95 |
| WHSV (weight hourly space velocity) (on the basis of ethylbenzene) | 4.0 $hr^{-1}$ |
| Reaction temperature | 350° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of ethylbenzene | 20% |
| Selectivity for diethylbenzenes based on converted ethylbenzene | 95% |
| Para-isomer in diethylbenzenes | 99.5% |

EXAMPLE 23

The catalyst as obtained in Example 22 was used for preparing ethyltoluene from toluene and ethylene. The reaction was carried out under the following reaction conditions:

| | |
|---|---|
| Toluene/ethylene/$H_2$ in molar ratio | 6/1/6 |
| WHSV (weight hourly space velocity) (on the basis of toluene) | 4.0 $hr^{-1}$ |
| Reaction pressure | 3.0 $kg/cm^2$ |
| Reaction temperature | 400° C. |
| Apparatus | Fixed bed Reactor |

The reaction products respectively obtained in a period between 2 hours after the beginning of the reaction and 3 hours after the beginning of the reaction, in a period between 20 hours after the beginning of the reaction and 21 hours after the beginning of the reaction and in a period between 60 hours after the beginning of the reaction and 61 hours after the beginning of the reaction were each collected and analyzed by gas chromatography. The results are summarized in Table 19 given below.

TABLE 19

| Trap time (hr) | Conversion of toluene (%) | Selectivity for ethyltoluenes based on converted toluene (%) | Each isomer in ethyltoluenes (%) | | |
|---|---|---|---|---|---|
| | | | p-isomer | m-isomer | o-isomer |
| 2–3 | 16 | 97 | 99.0 | 0.9 | 0.1 |
| 20–21 | 15 | 97 | 99.2 | 0.8 | 0 |
| 60–61 | 14 | 97 | 99.4 | 0.6 | 0 |

EXAMPLE 24

The catalyst as obtained in Example 22 was used for disproportionation reaction of toluene. The reaction was carried out under the following reaction conditions:

| | |
|---|---|
| $H_2$/toluene in molar ratio | 2.5 |
| WHSV (weight hourly space velocity) (on the basis of toluene) | 2.0 $hr^{-1}$ |
| Reaction temperature | 500° C. |
| Reaction pressure | 10 $kg/cm^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 20 given below.

TABLE 20

| Trap time (hr) | Conversion of toluene (%) | Selectivity for each product based on converted toluene (mol %) | | | Each isomer in xylenes (%) | | |
|---|---|---|---|---|---|---|---|
| | | benzene | xylene | ethylbenzene | p-isomer | m-isomer | o-isomer |
| 2–3 | 20 | 53.0 | 45.9 | 0.9 | 96.0 | 3.2 | 0.8 |
| 20–21 | 20 | 52.8 | 46.5 | 0.5 | 96.5 | 3.3 | 0.2 |

EXAMPLE 25

The catalyst as obtained in Example 22 was used for preparing xylene from toluene and methanol. The reaction was carried out under the following reaction conditions:

| | |
|---|---|
| Toluene/methanol in molar ratio | 2 |
| WHSV (weight hourly space velocity) (on the basis of toluene) | 4.0 $hr^{-1}$ |
| Reaction temperature | 450° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of toluene | 35% |

-continued

| | |
|---|---|
| Selectivity for xylenes based on converted toluene | 95% |
| Each isomer in xylenes: | |
| para-isomer | 97% |
| meta-isomer | 2% |
| ortho-isomer | 1% |

EXAMPLE 26

The ion-exchanged crystalline chromosilicate H-AZ-3 as obtained in Example 22 was formed into 10 to 20 mesh particles and filled in a reaction tube made of a glass. Through the reaction tube was passed a nitrogen gas containing 25% by volume of tetramethoxysilane at 320° C. and at an SV of 1500 hr$^{-1}$ for 20 minutes. Then, air was passed through the tube at 500° C. for 20 minutes to effect the calcination of the treated AZ-1.

The amount of silica supported on H-AZ-3 by the above mentioned treatment was 1.0 wt % based on the weight of the untreated H-AZ-3. The thus obtained treated H-AZ-3 was used as a catalyst for preparing diethylbenzene from ethylbenzene and ethylene. The reaction was carried out under the following reaction conditions:

| | |
|---|---|
| Ethylbenzene/ethylene/H$_2$ in molar ratio | 5/1/4 |
| WHSV (weight hourly space velocity) (on the basis of ethylbenzene) | 4.0 hr$^{-1}$ |
| Reaction temperature | 350° C. |
| Reaction pressure | 3 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 21 given below.

TABLE 21

| Trap time (hr) | Conversion of ethyl-benzene (%) | Selectivity for diethylbenzenes based on converted ethyl-benzene (%) | Each isomer in diethylbenzenes | | |
|---|---|---|---|---|---|
| | | | p-isomer | m-isomer | o-isomer |
| 2–3 | 22 | 93 | 98.2 | 1.5 | 0.3 |
| 20–21 | 21 | 94 | 98.6 | 1.2 | 0.2 |

EXAMPLE 27

The catalyst as obtained in Example 26 was used for disproportionation reaction of toluene. The reaction was carried out under the following reaction conditions:

| | |
|---|---|
| H$_2$/toluene in molar ratio | 3.0 |
| WHSV (weight hourly space velocity) (on the basis of toluene) | 3.0 hr$^{-1}$ |
| Reaction temperature | 480° C. |
| Reaction pressure | 8.0 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas choromatography. The cresults are summarized in Table 22 given below.

TABLE 22

| Trap time (hr) | Conversion of toluene (%) | Selectivity for each product based on converted toluene (mol %) | | | Each isomer in xylenes (%) | | |
|---|---|---|---|---|---|---|---|
| | | Benzene | Xylene | Ethylbenzene | p-isomer | m-isomer | o-isomer |
| 2–3 | 14 | 52.2 | 46.3 | 1.0 | 95.5 | 3.0 | 1.5 |
| 20–21 | 14 | 52.4 | 46.5 | 0.9 | 96.0 | 3.0 | 1.0 |

EXAMPLE 28

The catalyst as obtained in Example 26 was used for preparing cymene from toluene and propylene. The reaction was carried out under the following reaction conditions:

| | |
|---|---|
| Toluene/propylene/H$_2$ in molar ratio | 5/1/4 |
| WHSV (weight hourly space velocity) (on the basis of toluene) | 8.0 hr$^{-1}$ |
| Reaction temperature | 320° C. |
| Reaction pressure | 2.0 kg/cm$^2$ |
| Apparatus | Fixed bed reactor |

The reaction product obtained in a period between 2 hous after the beginning of the reaction and 3 hours after the beginning of the reaction and the reaction product obtained in a period between 10 hours after the beginning of the reaction and 11 hours after the beginning of the reaction were each collected and analyzed by gas chromatography. The results are summarized in Table 23 given below.

TABLE 23

| Trap Time [hr] | Conversion of toluene [%] | Selectivity for cymenes based on converted toluene (%) | Each isomer in cymenes | | |
|---|---|---|---|---|---|
| | | | p-iso-mer | m-iso-mer | o-iso-mer |
| 2–3 | 13 | 90 | 96.0 | 3.8 | 0.2 |
| 10–11 | 13 | 91 | 97.0 | 3.0 | 0 |

EXAMPLE 29

In 400 g of water were dissolved 250 g of 1,8-diamino-4-aminomethyloctane, 10 g of chromiun nitrate [Cr(NO$_3$)$_3$.9H$_2$O] and 10 g of sodium hydroxide, and was further added 500 g of a silica sol (SiO$_2$ content: 30% by weight) to obtain a uniform solution. To the solution was dropwise added 50 g of a 20% aqueous solution of sulfuric acid to obtain a uniform gel. The obtained gel was put in a homogenizer and kneaded at a speed of 8000 rpm. Then, the gel was put in a polytetrafluoroethylene-lined autoclave and allowed to stand at 160° C. for 70 hours to effect crystallization.

Figure 9:
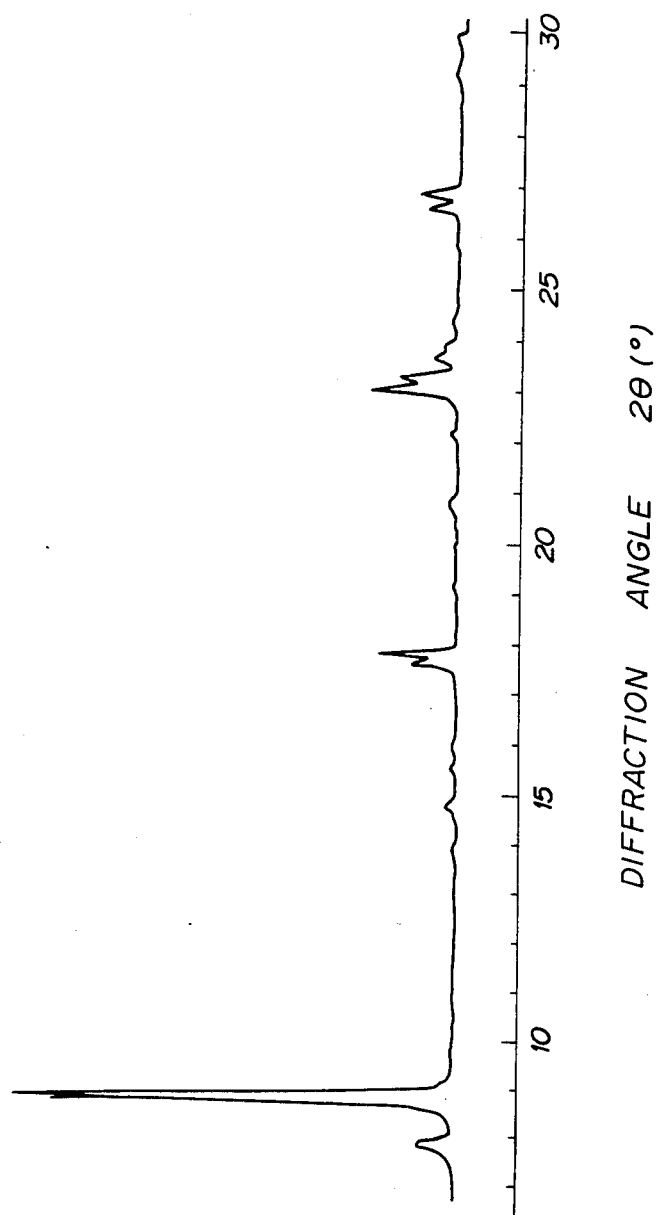
FIG. 9 is an X-ray diffraction pattern of another form of a crystalline chromosilicate zeolite AZ-3 which may be used as a precursor of the catalyst to be used in the process of the present invention.

The obtained product was filtered off, washed and dried at 120° C. for 4 hours and calcined at 500° C. for 8 hours. The product was subjected to X-ray diffractometry to obtain an X-ray diffraction pattern as shown in FIG. 9. From the diffraction pattern, the product was identified as a crystalline chromosilicate AZ-3.

The thus obtained AZ-3 was subjected to ion-exhange in a 0.5 N hydrochloric acid for 24 hours. Then, the product was filtered off, washed and dried at 120° C. for 4 hours and calcined in air at 500° C. for 4 hours to obtain an ion-exchanged AZ-3 (H-AZ-3). The product had an $SiO_2/Cr_2O_3$ molar ratio of 40 and a constraint index of 13.0 as measured at 325° C. and contained H+ *as a cation in an amount of* 90% based on the ion-exchange capacity.

20 g of the obtained H-AZ-3 was formed into 10 to 20 mesh particles and filled in a reaction tube made of a glass. Through the reaction tube was passed a nitrogen gas containing 10% by volume of tetraethoxysilane at 250° C. and at an SV of 1000 hr$^{-1}$ for 15 minutes. Then, air was pass through the tube at 550° C. for 4 hours to effect the calcination of the treated H-AZ-3.

The amount of silica supported on H-AZ-3 by the above-mentioned treatment was 1.5 wt % based on the weight of the untreated H-AZ-3.

The thus obtained treated H-AZ-3 was used as a catalyst for disproportionation reaction of ethylbenzene. The reaction was carried out under the following reaction conditions:

| | |
|---|---|
| H$_2$/ethylbenzene in molar ratio | 4.0 |
| WHSV (weight hourly space velocity) (on the basis of ethylbenzene) | 5.0 hr$^{-1}$ |
| Reaction temperature | 350° C. |
| Reaction pressure | 3.0 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 24 given below.

TABLE 24

| Trap time (hr) | Conversion of ethylbenzene (%) | Selectivity for each product based on converted ethylbenzene (mol %) | | Each isomer in diethylbenzenes (%) | | |
|---|---|---|---|---|---|---|
| | | Benzene | Diethylbenzenes | p-isomer | m-isomer | o-isomer |
| 2–3 | 50 | 54.9 | 44.8 | 99.4 | 0.6 | 0 |
| 20–21 | 50 | 54.9 | 45.1 | 100 | 0 | 0 |

EXAMPLE 30

The catalyst as obtained in Example 29 was used for preparing ethyltoluene from toluene and ethylene. The preparation reaction was carried out under the following reaction conditions:

| | |
|---|---|
| Toluene/ethylene H$_2$ in molar ratio | 5/1/5 |
| WHSV (weight hourly space velocity) (on the basis of toluene) | 3.0 hr$^{-1}$ |
| Reaction pressure | 4.0 kg/cm$^2$ |
| Reaction temperature | 420° C. |
| Apparatus | Fixed bed reactor |

The reaction product obtained in a period between 2 hours after the beginning of the reaction and 3 hours after the beginning of the reaction and the reaction product obtained in a period between 12 hours after the beginning of the reaction and 13 hours after the beginning of the reaction were each collected and analyzed by gas chromatography. The results are summarized in Table 25 given below.

TABLE 25

| Trap time (hr) | Conversion of toluene (%) | Selectivity for ethyltoluenes based on converted toluene (%) | Each isomer in ethyltoluene (%) | | |
|---|---|---|---|---|---|
| | | | p-isomer | m-isomer | o-isomer |
| 2–3 | 20 | 98 | 98.5 | 0.9 | 0.6 |
| 12–13 | 20 | 98 | 99.0 | 0.7 | 0.3 |

EXAMPLE 31

To 25 g water were added 2.0 g of chromium nitrate [Cr(NO$_3$)$_3$.9H$_2$O], 2.0 g of morpholine and 1.76 g of a 96% aqueous solution of sulfuric acid to give a solution. The resulting solution was dropwise added little by little to a solution containing 7.9 g of sodium chloride dissolved in 12.2 g of water. To the resulting mixture was added drop by drop a solution containing 20 g of a water glass (SiO$_2$ content, 37.6% by weight; Na$_2$O content, 17.5% by weight; water content, 44.9% by weight) dissolved in 30 g of water to obtain a uniform mixture.

The obtained mixture was put in a polytetrafluoroethylene-lined autoclave and subjected to crystallization at 170° C. for 24 hours while stirring.

Figure 10:
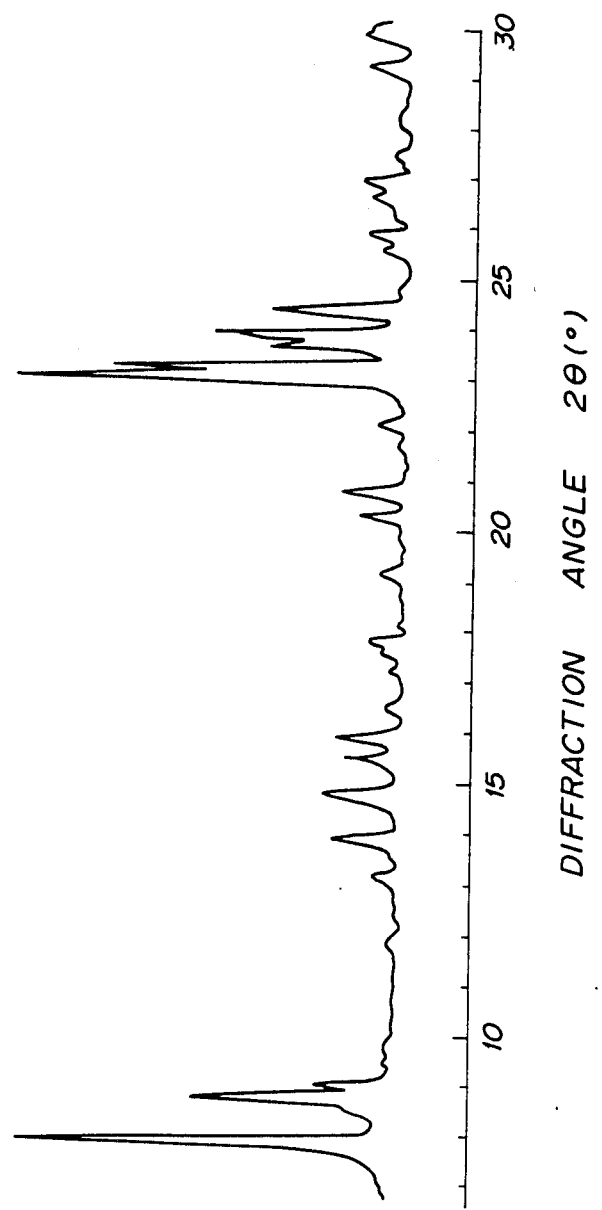
FIG. 10 is an X-ray diffraction pattern of a crystalline ZSM-5-like chromosilicate zeolite which may be used as a precursor of the catalyst to be used in the process of the present invention.

The obtained product was filtered off, washed and dried at 120° C. for 6 hours and calcined in air at 500° C. for 6 hours. The product was subjected to X-ray diffractometry. The obtained X-ray diffraction pattern is shown in FIG. 10. The obtained pattern was substantially in agreement with that of a crystalline aluminosilicate ZSM-5 and was identified as a ZSM-5-like chromosilicate disclosed in Japanese Patent Application Laid-Open Specification Nos. 57-7817 and 57-169434. The product was subjected to fluorescent X-ray analysis and found to have a SiO$_2$/Cr$_2$O$_3$ molar ratio of 60. The product had a consraint index of 10.0 as measured at 330° C. and contained H+ as a cation in an amount of 93% based on the ion-exchange capacity.

10 g of the obtained crystalline chromosilicate was formed into 10 to 20 mesh particles and filled in a reaction tube made of a glass. In the reaction tube, the chromosilicate was contacted with a vapor of tetraethoxysilane under a pressure of 50 mmHg at 250° C. for 30 minutes. Then, air was passed through the tube at 500° C. for 3 hours to effect the calcination of the treated chromosilicate.

The amount of silica supported on chromosilicate by the above-mentioned treatment was 3.0 wt % based on the weight of the untreated chromosilicate.

The thus obtained treated chromosilicate was used as a catalyst for preparing diethylbenzene from ethylbenzene and ethylene. The reaction was carried out under the following reaction conditions:

| | |
|---|---|
| Ethylbenzene/ethylene/H$_2$ in molar ratio | 5/1/4 |
| WHSV (weight hourly space velocity) (on the basis of ethylbenzene) | 4.0 hr$^{-1}$ |
| Reaction temperature | 350° C. |
| Reaction pressure | 3 kg/cm$^2$ |
| Apparatus | Fixed bed reactor |

The reaction product obtained in a period between 2 hours after the beginning of the reaction and 3 hours after the beginning of the reaction and the reaction product obtained in a period between 20 hours after the beginning of the reaction and 21 hours after the beginning of the reaction were each collected and analyzed by gas chromatography. The results are summarized in Table 26 given below.

TABLE 26

| Trap time (hr) | Conversion of ethylbenzene (%) | Selectivity for diethylbenzenes based on converted ethylbenzene (%) | Each isomer in diethylbenzenes (%) | | |
|---|---|---|---|---|---|
| | | | p-isomer | m-isomer | o-isomer |
| 2–3 | 23 | 88 | 95.0 | 4.0 | 1.0 |
| 20–21 | 21 | 89 | 95.2 | 4.0 | 0.8 |

EXAMPLE 32

The catalyst as obtained in Example 1 was used for alkylation of benzene with ethylene. The alkylation reaction was carried out under the following conditions:

| | |
|---|---|
| Benzene/ethylene/H$_2$ in molar ratio | 4/1/4 |
| WHSV (weight hourly space velocity) (on the basis of benzene) | 4.0 hr$^{-1}$ |
| Reaction temperature | 400° C. |
| Reaction pressure | 3.0 kg/cm$^2$ |
| Apparatus | Fixed bed reactor |

The products were analyzed at the respective ends of the operating periods as indicated in Table 27. The results are summarized in Table 27.

TABLE 27

| Trap time (hr) | Conversion of benzene (%) | Selectivity for each product based on converted benzene (%) | | | | | | | Each isomer in diethylbenzenes (%) | | |
|---|---|---|---|---|---|---|---|---|---|---|---|
| | | ethylbenzene | toluene | xylenes | cumene | n-propyl-benzene | ethyltoluenes | diethylbenzenes | p-isomer | m-isomer | o-isomer |
| 3 | 22.4 | 87.4 | 0.63 | 0.01 | 0.20 | 1.50 | 0.20 | 10.06 | 98.0 | 1.8 | 0.2 |
| 10 | 22.1 | 87.1 | 0.64 | 0.01 | 0.20 | 1.48 | 0.20 | 10.37 | 98.2 | 1.7 | 0.1 |

EXAMPLE 33

The catalyst as obtained in Example 22 was used for alkylation of benzene with ethylene. The alkylation reaction was carried out under the following conditions:

| | |
|---|---|
| Benzene/ethylene/H$_2$ | 5/1/3 |
| WHSV (weight hourly space velocity) (on the basis of benzene) | 4.0 hr$^{-1}$ |
| Reaction temperature | 420° C. |
| Reaction pressure | 3.0 kg/cm$^2$ |
| Apparatus | Fixed bed reactor |

The products were analyzed at the respective ends of the operation periods as indicated in Table 28. The results are summarized in Table 28.

TABLE 28

| Trap time (hr) | Conversion of benzene (%) | Selectivity for each product based on converted benzene (%) | | | | | | | Each isomer in diethylbenzenes (%) | | |
|---|---|---|---|---|---|---|---|---|---|---|---|
| | | ethylbenzene | toluene | xylenes | cumene | n-propyl-benzene | ethyltoluenes | diethylbenzenes | p-isomer | m-isomer | o-isomer |
| 2 | 18.3 | 89.00 | 0.31 | 0.01 | 0.18 | 0.60 | 0.18 | 9.72 | 98.3 | 1.6 | 0.1 |
| 12 | 18.0 | 89.02 | 0.30 | 0.01 | 0.18 | 0.58 | 0.17 | 9.74 | 98.4 | 1.5 | 0.1 |

EXAMPLE 34

The catalyst as obtained in Example 1 was used for preparing ethyltoluene from toluene and ethanol. The reaction was carried out under the following experimental conditions:

| | |
|---|---|
| Toluene/ethanol in molar ratio | 3/1 |
| WHSV (weight hourly space velocity) (on the basis of toluene) | 5.0 hr$^{-1}$ |
| Reaction temperature | 400° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of toluene | 20% |
| Selectivity for ethyltoluenes based on converted toluene | 92% |
| Para-isomer in ethyltoluenes | 98% |

EXAMPLE 35

20 g of AZ-1 as obtained in Example 8 was formed into 10 to 20 mesh particles and packed in a reaction tube made of a glass. Through the reaction tube was passed a nitrogen gas containing 7% by volume of tetran-propoxysilane at 300° C. and at an SV (space velocity) of 2000 hr$^{-1}$ for 15 minutes. Then, air was passed through the tube at 500° C. for 4 hours to effect the calcination of the treated AZ-1.

The amount of silica supported on AZ-1 by the above-mentioned treatment was 0.6 wt % based on the weight of the untreated AZ-1.

The thus obtained treated AZ-1 was used as a catalyst for preparing diethylbenzene from ethylbenzene and ethylene. The reaction was carried out under the following reaction conditions:

| | |
|---|---|
| Ethylbenzene/ethylene in molar ratio | 4/1 |
| WHSV (weight hourly space velocity) (on the basis of ethylbenzene) | 3.0 hr$^{-1}$ |
| Reaction temperature | 350° C. |
| Reaction pressure | Atmospheric |
| Apparatus | Fixed bed reactor |

The reaction product obtained in a period between 3 hours after the beginning of the reaction and 4 hours after the beginning of the reaction was collected and analyzed by gas chromatography. The results are summarized below.

| | |
|---|---|
| Conversion of ethylbenzene | 12% |
| Selectivity for diethylbenzenes based on converted ethylbenzene | 93% |
| Para-isomer in diethylbenzenes | 95.5% |

EXAMPLE 36

20 g of AZ-1 as obtained in Example 8 was formed into 10 to 20 mesh particles and packed in a reaction tube made of a glass. Through the reaction tube was passed a nitrogen gas containing 8.5% by volume of tetra-iso-propoxysilane at 250° C. and at an SV (space velocity) of 3500 hr$^{-1}$ for 12 minutes. Then, air was passed through the tube at 500° C. for 3 hours to effect the calcination of the treated AZ-1.

The amount of silica supported on AZ-1 by the above-mentioned treatment was 0.2 wt % based on the weight of the untreated AZ-1.

The thus obtained treated AZ-1 was used as a catalyst for preparing diethylbenzene from ethylbenzene and ethylene. The reaction was carried out under the following reaction conditions:

| | |
|---|---|
| Ethylbenzene/ethylene in molar ratio | 3/1 |
| WHSV (weight hourly space velocity) (on the basis of ethylbenzene) | 4.0 hr$^{-1}$ |
| Reaction temperature | 370° C. |
| Reaction pressure | Atmospheric |
| Apparatus | Fixed bed reactor |

The reaction product obtained in a period between 4 hours after the beginning of the reaction and 5 hours after the beginning of the reaction was collected and analyzed by gas chromatography. The results are summarized below.

| | |
|---|---|
| Conversion of ethylbenzene | 20% |
| Selectivity for diethylbenzenes based on converted ethylbenzene | 91% |
| Para-isomer in diethylbenzenes | 96.5% |

EXAMPLE 37

10 g of the ion-exchanged crystalline chromosilicate H-AZ-3 as obtained in Example 22 was formed into 10 to 20 mesh particles and packed in a reaction tube made of a glass. Through the reaction tube was passed a nitrogen gas containing 15% by volume of tetra-n-butoxysilane at 320° C. and at an SV (space velocity) of 1200 hr$^{-1}$ for 20 minutes. Then, air was passed through the tube at 500° C. for 4 hours to effect the calcination of the treated H-AZ-3.

The amount of silica supported on H-AZ-3 by the above-mentioned treatment was 0.8 wt % based on the weight of the untreated H-AZ-3.

The thus obtained treated H-AZ-3 was used as a catalyst for preparing diethylbenzene from ethylbenzene and ethylene. The reaction was carried out under the following reaction conditions:

| | |
|---|---|
| Ethylbenzene/ethylene in molar ratio | 4/1 |
| WHSV (weight hourly space velocity) (on the basis of ethylbenzene) | 4.0 hr$^{-1}$ |
| Reaction temperature | 350° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of ethylbenzene | 18% |
| Selectivity for diethylbenzenes based on converted ethylbenzene | 93% |
| Para-isomer in diethylbenzenes | 97% |

EXAMPLE 38

10 g of the ion-exchanged crystalline chromosilicate H-AZ-3 as obtained in Example 22 was formed into 10 to 20 mesh particles and packed in a reaction tube made of a glass. Through the reaction tube was passed a nitrogen gas containing 20% by volume of tetra-tert-butoxysilane at 300° C. and at an SV (space velocity) of 2500 hr$^{-1}$ for 15 minutes. Then, air was passed through the tube at 500° C. for 2 hours to effect the calcination of the treated H-AZ-3.

The amount of silica supported on H-AZ-3 by the above-mentioned treatment was 1.2 wt % based on the weight of the untreated H-AZ-3.

The thus obtained treated H-AZ-3 was used as a catalyst for preparing diethylbenzene from ethylbenzene and ethylene. The reaction was carried out under the following reaction conditions:

| | |
|---|---|
| Ethylbenzene/ethylene in molar ratio | 3/1 |
| WHSV (weight hourly space velocity) (on the basis of ethylbenzene) | 4.0 hr$^{-1}$ |
| Reaction temperature | 360° C. |
| Reaction pressure | Atmospheric |
| Apparatus | Fixed bed reactor |

The reaction product obtained in a period between 2 hours after the beginning of the reaction and 3 hours after the beginning of the reaction was collected and analyzed by gas chromatography. The results are summarized below.

| | |
|---|---|
| Conversion of ethylbenzene | 22% |
| Selectivity for diethylbenzenes based on converted ethylbenzene | 92% |
| Para-isomer in diethylbenzenes | 98% |

COMPARATIVE EXAMPLE

Preparation of ethyltoluene from toluene and ethylene was effected using, as catalysts, AZ-1, ZSM-5, ZSM-11, H-AZ-2, ZSM-5-like borosilicate, H-AZ-3 and ZSM-5-like chromosilicate as obtained in Examples 1, 11, 12, 13, 21, 22 and 31, respectively. The reaction was carried out under the following reaction conditions:

| | |
|---|---|
| Toluene/ethylene/H$_2$ in molar ratio | 4/1/4 |
| WHSV (weight hourly space velocity) (on the basis of toluene) | 4.0 hr$^{-1}$ |
| Reaction temperature | 400° C. |
| Reaction pressure | 3.0 kg/cm$^2$ |
| Apparatus | Fixed bed reactor |

The reaction product obtained in a period between 4 hours after the beginning of the reaction and 5 hours after the beginning of the reaction was collected and analyzed by gas chromatography. The results are summarized in Table 29 given below.

TABLE 29

| Catalyst | Conversion of toluene (%) | Selectivity for ethyltoluenes based on converted toluene (%) | Each isomer in ethyltoluenes (%) | | |
|---|---|---|---|---|---|
| | | | p-isomer | m-isomer | o-isomer |
| AZ-1 | 26 | 97 | 85 | 12 | 3 |
| ZSM-5 | 27 | 92 | 35 | 57 | 8 |
| ZSM-11 | 24 | 91 | 30 | 60 | 10 |
| H-AZ-2 | 25 | 98 | 80 | 16 | 4 |
| ion-exchanged ZSM-5-like borosilicate | 26 | 93 | 40 | 54 | 6 |
| H-AZ-3 | 25 | 97 | 86 | 12 | 2 |
| ZSM-5-like chromosilicate | 24 | 93 | 45 | 50 | 5 |

What is claimed is:

1. A process for producing a 1,4-dialkylbenzene which comprises contacting benzene or a monoalkylbenzene with an alkylating agent in the vapor phase in the presence of a catalyst obtained by subjecting a zeolite to a treatment with a gas containing a silicic acid ester and then a calcination in an oxygen-containing gas, said zeolite being a metallosilicate having a molar ratio of SiO$_2$/X$_2$O$_3$ in which X is at least one member selected from the group consiting of Al, B and Cr, of 10 or more and having a constraint index within the range of 1 to 15.

2. A process according to claim 1, wherein said contact of benzene or a monoalkylbenzene with an alkylating agent is effected in the copresence of hydrogen.

3. A process according to claim 1, wherein said zeolite is a crystalline aluminosilicate having in its X-ray diffraction pattern obtained by using CuKα line at least seven diffraction lines showing the following relative intensities at the positions of the following respective diffraction angles (2θ):

| Diffraction angle (2θ,deg) | Relative intensity |
|---|---|
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 | taking the intensity of the diffraction line at a diffraction angle of 8.7°±0.2° or 8.9°±0.2° as 100.

4. A process according to claim 1, wherein said zeolite is a crystalline borosilicate having in its X-ray diffraction pattern obtained by using CuKα line at least eight diffraction lines showing the following relative intensities at the positions of the following respective diffraction angles (2θ):

| Diffraction angle (2θ, deg) | Relative intensity |
|---|---|
| 7.9 ± 0.2 | 10–50 |
| 8.9 ± 0.2 | 100 |
| 17.7 ± 0.2 | 5–30 |
| 17.9 ± 0.2 | 5–30 |
| 23.2 ± 0.2 | 20–80 |
| 23.4 ± 0.2 | 20–60 |
| 26.7 ± 0.2 | 2–20 |
| 27.0 ± 0.2 | 2–20 | taking the intensity of the diffraction line at a diffraction angle of 8.9°±0.2° as 100.

5. A process according to claim 1, wherein said zeolite is a crystalline chromosilicate having in its X-ray diffraction pattern obtained by using CuKα line at least nine diffraction lines showing the following relative intensities at the positions of the following respective diffraction angles (2θ):

| Diffraction angle (2θ, deg) | Relative intensity |
|---|---|
| 7.9 ± 0.2 | 2–10 |
| 8.8 ± 0.2 | 75–100 |
| 8.9 ± 0.2 | 75–100 |
| 17.6 ± 0.2 | 5–25 |
| 17.8 ± 0.2 | 5–25 |
| 23.0 ± 0.2 | 10–28 |
| 23.3 ± 0.2 | 10–25 |
| 26.6 ± 0.2 | 2–20 |
| 26.8 ± 0.2 | 2–20 | taking the intensity of the diffraction line at a diffraction angle of 8.8°±0.2° or 8.9°±0.2° as 100.

6. A process according to claim 1, wherein said monoalkylbenzene has an alkyl group having 1 to 3 carbon atoms.

7. A process according to claim 1, wherein said dialkylbenzene is selected from the group consisting of para-xylene, para-ethyltoluene and para-diethylbenzene.

8. A process according to claim 1, wherein said alkylating agent is selected from the group consisting of ethylene, propylene, methanol and ethanol.

9. A process according to claim 1, wherein said silicic acid ester is selected from the group consisting of tetramethoxysilane, tetraethoxysilane, tetra-n-propoxysilane, tetra-iso-propoxysilane, tetra-n-butoxysilane and tetra-tertbutoxysilane.

10. A process according to claim 1 wherein the zeolite has a molar ratio of SiO$_2$/Al$_2$O$_3$ of from 10 to 1,000.

11. A process according to claim 1 wherein the zeolite has a molar ratio of SiO$_2$/B$_2$O$_3$ of from 10 to 1,000.

12. A process according to claim 1 wherein the zeolite has a molar ratio of SiO$_2$/Cr$_2$O$_3$ of from 10 to 1,000.

* * * * *